US008614295B2

(12) United States Patent
Lawson et al.

(10) Patent No.: US 8,614,295 B2
(45) Date of Patent: Dec. 24, 2013

(54) ANTIBODY MOLECULES HAVING SPECIFICITY FOR HUMAN OX40

(75) Inventors: Alastair David Griffiths Lawson, Slough (GB); Andrew Malcolm Nesbitt, Slough (GB); Andrew George Popplewell, Slough (GB); Stevan Graham Shaw, Slough (GB); Diana Shpektor, Shoreline, WA (US); Yi Zhang, San Francisco, CA (US)

(73) Assignee: UCB Pharma S.A. (BE)

( * ) Notice: Subject to any disclaimer, the term of this patent is extended or adjusted under 35 U.S.C. 154(b) by 363 days.

(21) Appl. No.: 12/706,993

(22) Filed: Feb. 17, 2010

(65) Prior Publication Data

US 2010/0254978 A1  Oct. 7, 2010

Related U.S. Application Data

(60) Provisional application No. 61/153,038, filed on Feb. 17, 2009.

(51) Int. Cl.
*C07K 16/00* (2006.01)
*A61K 39/395* (2006.01)
*C07H 21/04* (2006.01)
*C12N 5/16* (2006.01)

(52) U.S. Cl.
USPC ............... 530/387.1; 424/130.1; 536/23.5; 435/320.1; 435/455

(58) Field of Classification Search
None
See application file for complete search history.

(56) References Cited

U.S. PATENT DOCUMENTS

| | | | |
|---|---|---|---|
| 4,741,900 A | 5/1988 | Alvarez et al. | |
| 5,219,996 A | 6/1993 | Bodmer et al. | |
| 5,223,409 A | 6/1993 | Ladner et al. | |
| 5,403,484 A | 4/1995 | Ladner et al. | |
| 5,427,908 A | 6/1995 | Dower et al. | |
| 5,516,637 A | 5/1996 | Huang et al. | |
| 5,545,806 A | 8/1996 | Lonberg et al. | |
| 5,569,825 A | 10/1996 | Lonberg et al. | |
| 5,571,698 A | 11/1996 | Ladner et al. | |
| 5,580,717 A | 12/1996 | Dower et al. | |
| 5,585,089 A | 12/1996 | Queen et al. | |
| 5,625,126 A | 4/1997 | Lonberg et al. | |
| 5,633,425 A | 5/1997 | Lonberg et al. | |
| 5,658,727 A | 8/1997 | Barbas et al. | |
| 5,661,016 A | 8/1997 | Lonberg et al. | |
| 5,677,425 A | 10/1997 | Bodmer et al. | |
| 5,698,426 A | 12/1997 | Huse | |
| 5,733,743 A | 3/1998 | Johnson et al. | |
| 5,750,753 A | 5/1998 | Kimae et al. | |
| 5,770,429 A | 6/1998 | Lonberg et al. | |
| 5,780,225 A | 7/1998 | Wigler et al. | |
| 5,821,047 A | 10/1998 | Garrard et al. | |
| 5,969,108 A | 10/1999 | McCafferty et al. | |
| 6,277,962 B1 | 8/2001 | Godfrey et al. | |
| 6,632,927 B2* | 10/2003 | Adair et al. | 530/387.3 |
| 7,291,331 B1 | 11/2007 | Croft et al. | |
| 7,531,170 B1 | 5/2009 | Croft et al. | |
| 7,807,156 B1 | 10/2010 | Croft et al. | |
| 7,960,515 B2 | 6/2011 | Min et al. | |
| 8,101,175 B1 | 1/2012 | Croft et al. | |
| 2004/0146948 A1 | 7/2004 | Britton et al. | |
| 2005/0181448 A1 | 8/2005 | Popplewell et al. | |
| 2007/0110747 A1 | 5/2007 | Paszty et al. | |
| 2007/0224627 A1 | 9/2007 | Horowitz et al. | |
| 2008/0069822 A1 | 3/2008 | Jensen et al. | |
| 2010/0136030 A1* | 6/2010 | Salah-Eddine et al. | 424/173.1 |

FOREIGN PATENT DOCUMENTS

| | | |
|---|---|---|
| EP | 0392745 B1 | 10/1990 |
| EP | 0438474 B1 | 7/1991 |
| EP | 0463151 B1 | 1/1992 |
| EP | 0546073 B1 | 6/1993 |
| EP | 0948544 B1 | 10/1999 |
| EP | 1090037 B1 | 4/2001 |
| WO | WO86/01533 A1 | 3/1986 |
| WO | WO89/00195 A1 | 1/1989 |
| WO | WO89/01476 A1 | 2/1989 |
| WO | WO90/02809 A1 | 3/1990 |
| WO | WO91/09967 A1 | 7/1991 |
| WO | WO91/10737 A1 | 7/1991 |
| WO | WO92/01047 A1 | 1/1992 |
| WO | WO92/02551 A1 | 2/1992 |
| WO | WO92/18619 A1 | 10/1992 |
| WO | WO92/22583 A2 | 12/1992 |
| WO | WO93/06231 A1 | 4/1993 |
| WO | WO93/11236 A1 | 6/1993 |
| WO | WO95/15982 A2 | 6/1995 |
| WO | WO95/20401 A1 | 8/1995 |
| WO | WO98/20734 A1 | 5/1998 |
| WO | WO98/25971 A1 | 6/1998 |
| WO | WO03/026693 A2 | 4/2003 |
| WO | WO03/031581 A2 | 4/2003 |
| WO | WO03/048208 A2 | 6/2003 |
| WO | WO03/059245 A2 | 7/2003 |

(Continued)

OTHER PUBLICATIONS

Paul. Fundamental Immunology, 3rd Edition, 1993, pp. 292-295.*
Rudikoff, Giusti, Cook, and Scharff. Single amino acid substitution altering antigen binding specificity. Proceedings of the National Academy of Sciences, 1982. vol. 79, pp. 1979-1983.*
Colman. Effects of amino acid sequence changes on antibody-antigen interactions. Research in Immunology, 1994. vol. 145, pp. 33-36.*
Mac Callum, Martin, and Thornton. Antibody-antigen interactions: contact analysis and binding site topography. Journal of Molecular Biology, 1996. vol. 262, pp. 732-745.*
De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanized monoclonal antibody. Journal of Immunology, 2002. vol. 169, pp. 3076-3084.*

(Continued)

*Primary Examiner* — Ilia Ouspenski
(74) *Attorney, Agent, or Firm* — Saul Ewing LLP; Doreen Y. Trujillo

(57) ABSTRACT

The invention relates to antibody molecules having specificity for antigenic determinants of human OX40, therapeutic uses of the antibody molecules and methods for producing said antibody molecules.

29 Claims, 10 Drawing Sheets

(56) References Cited

FOREIGN PATENT DOCUMENTS

| WO | 2004035619 | 4/2004 |
|---|---|---|
| WO | WO2004/051268 A1 | 6/2004 |
| WO | WO2004/072116 A2 | 8/2004 |
| WO | WO2004/106377 A1 | 12/2004 |
| WO | WO2005/003169 A2 | 1/2005 |
| WO | WO2005/003170 A2 | 1/2005 |
| WO | WO2005/003171 A2 | 1/2005 |
| WO | WO2005/061540 A2 | 7/2005 |
| WO | WO2005/113605 A1 | 12/2005 |
| WO | WO2005/117984 A2 | 12/2005 |
| WO | WO2006/029879 A2 | 3/2006 |
| WO | WO2006/131951 | 12/2006 |
| WO | WO2006/131951 A2 | 12/2006 |
| WO | 2007010231 | 1/2007 |
| WO | WO2007/003898 A1 | 1/2007 |
| WO | WO2007/062245 A2 | 5/2007 |
| WO | 2007065433 | 6/2007 |
| WO | WO2007/111931 A2 | 10/2007 |
| WO | WO2008/106116 A2 | 9/2008 |
| WO | WO2009/040562 A1 | 4/2009 |
| WO | WO2009/079335 A1 | 6/2009 |

OTHER PUBLICATIONS

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

Vajdos, Adams, Breece, Presta, De Vos, and Sidhu. Comprehensive functional maps of the antigen-binding site of an Anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Panka et al., 1988, Proc. Natl. Acad. Sci. USA, 85: 3080-3084.*

Rentero et al., Chimia 2011, 65: 843-845.*

Hungarian Intellectual Property Office, Search Report, Nov. 15, 2012, 18 pages (filed by Applicant on Apr. 19, 2013).*

Supplementary European Search Report, Mar. 22, 2013, 7 pages (filed by Applicant on Apr. 19, 2013).*

Adair, J.R., et al., "Therapeutic antibodies", Drug Design Reviews-Online, vol. 2, No. 3, pp. 209-217, 2005.

Altschul, S.F., et al., "Basic local alignment search tool", J. Mol. Biol., vol. 215, No. 3, pp. 403-410, 1990.

Altschul, S.F., et al., "Gapped BLAST and PSI-BLAST: a new generation of protein database search programs", Nucleic Acids Res., vol. 25, pp. 3389-3402, 1997.

Ames, R.S., et al., "Conversion of murine Fabs isolated from a combinatorial phage display library to full length immunoglobulins", J. Immunol. Methods, vol. 184, No. 2, pp. 177-186, 1995.

Angal, S., et al. "A single amino acid substitution abolishes the heterogeneity of chimeric mouse/human (IgG4) antibody", Molecular Immunology, vol. 30, No. 1, pp. 105-108, 1993.

Arestides, R.S., et al., "Costimulatory molecule OX40L is critical for both Th1 and Th2 responses in allergic inflammation", Eur. J. Immunol., vol. 32, pp. 2874-2880, 2002.

Babcook, J., et al., "A novel strategy for generating monoclonal antibodies from single, isolated lymphocytes producing antibodies of defined specificities", Proc. Natl. Acad. Sci. USA, vol. 93, No. 15, pp. 7843-7848, 1996.

Bach, F., et al., "Lymphocyte Interaction: A Potential Histocompatibiliy Text in vitro", Science, vol. 143, No. 3608, pp. 813-814, 1964.

Bansal-Pakala, P., et al., "Costimulation of CD8 T Cell Responses by OX40", J. Immunol, vol. 172, pp. 4821-4825, 2004.

Bishop, N. C., et al., "Lymphocyte responses to influenza and tetanus toxoid in vitro following intensive exercise and carbohydrate ingestion on consecutive days", J Appl Physiol, vol. 99, pp. 1327-1335, 2005.

Bodmer, J.L., et al., "The molecular architecture of the TNF superfamily", Trends Biochem Sci,, vol. 27, pp. 19-26, 2002.

Brinkmann, U., et al., "Phage Display of Disulfide-Stabilized FV Fragments", J. Immunol. Methods, vol. 182, No. 1, pp. 41-50, 1995.

Bromelow, K.V., et al., "Whole Blood Assay for Assessment of the Mixed Lymphocyte Reaction", J. Immunol. Methods, vol. 247, pp. 1-8, 2001.

Brugnoni, D., et al., "CD134/OX40 Expression by Synovial Fluid CD4+ T Lymphocytes in Chronic Synovitis", British Journal of Rheumatology., vol. 37, pp. 584-585, 1998.

Burgess, J.K., et al., "CD40 and OX40 ligand are increased on stimulated asthmatic airway smooth muscle", J. Allergy Clin Immunol., vol. 115, No. 2, pp. 302-308, 2005.

Burton, D.R., et al., "Human Antibodies from Combinatorial Libraries", Advances in Immunology, vol. 57, pp. 191-280, 1994.

Carboni, S., et al., "CD134 plays a crucial role in the pathogenesis of EAE and is upregulated in the CNS of patients with multiple sclerosis", J. Neuroimmunology, vol. 145, Nos. 1-2, pp. 1-11, 2003.

Chan, F.K., et al., "A domain in TNF receptors that mediates ligand-independent receptor assembly and signaling", Science, vol. 288, No. 5475, pp. 2351-2354, 2000.

Chapman, A., "PEGylated antibodies and antibody fragments for improved therapy: a review", Advanced Drug Delivery Reviews, vol. 54, pp. 531-545, 2002.

Chothia, C. and Lesk, A.M., Canonical Structures for the Hypervariable Regions of Immunoglobulins, J. Mol. Biol., vol. 196, pp. 901-917, 1987.

Cole, S.P.C., et al., "The EBV-hybridoma technique and its application to human lung cancer", Monoclonal Antibodies and Cancer Therapy, pp. 77-96, Alan R. Liss, Inc., 1985.

Compaan, D.M., et al., "The Crystal Structure of the Costimulatory OX40-OX40L Complex", Structure, vol. 14, pp. 1321-1330, 2006.

Dubowchik, G.M., et al., "Receptor-mediated and enzyme-dependent targeting of cytotoxic anticancer drugs", Pharmacology and Therapeutics, vol. 83, No. 2, pp. 67-123, 1999.

Giacomelli, R., et a., "T lymphocytes in the synovial fluid of patients with active rheumatoid arthritis display CD134-OX40 surface antigen", Clin. Exp. Rheumatol., vol. 19, No. 3, pp. 317-320, 2001.

Gish, W., et al., "Identification of protein coding regions by database similarity search", Nature Genet., vol. 3, pp. 266-272, 1993.

Gramaglia, I., et al., "Ox-40 Ligand: A Potent Costimulatory Molecule for Sustaining Primary CD4 T Cell Responses", J. Immunol., vol. 161, pp. 6510-6517, 1998.

Gramaglia, I., et al., "The OX40 Costimulatory Receptor Determines the Development of CD4 Memory by Regulating Primary Clonal Expansion", J. Immunol, vol. 165, pp. 3043-3050, 2000.

Harris, J.M. and Zalipsky, S., eds., Poly(ethylene glycol) Chemistry and Biological Applications, American Chemical Society, Chapter 11, "Conjugation of High-Molecular Weight Poly(ethylene glycol) to Cytokines: Granulocyte-Macrophage Colony-Stimulating Factors as Model Substrates", pp. 155-169, Washington, DC, 1997.

Harris, R.J., "Processing of C-terminal lysine and arginine residues of proteins isolated from mammalian cell culture", Journal of Chromatography, vol. 705, No. 1, pp. 129-134, 1995.

Hellstrom, K.E., et al., "Antibodies for Drug Delivery", Controlled Drug Delivery, $2^{nd}$ Ed.., Robinson et al., eds., pp. 623-653, Marcel Dekker, Inc., 1987.

Hieter, P.A., et al., "Evolution of Human Immunoglobulin K J Region Genes", J. Biol. Chem., vol. 257, No. 3, pp. 1516-1522, 1982.

Holliger, P., et al., "Engineered antibody fragments and the rise of single domains", Nature Biotechnology, vol. 23, No. 9, pp. 1126-1136, 2005.

(56) References Cited

OTHER PUBLICATIONS

Hoshino, A., et al., "Critical role for OX40 ligand in the development of pathogenic Th2 cells in a murine model of asthma", Eur. J. Immunol., vol. 33, No. 4, pp. 861-869, 2003.

Humphreys, D.P., et al., "A plasmid system for optimization of Fab production in *Escherichia coli*: importance of balance of heavy chain and light chain synthesis", Protein Expression and Purification, vol. 26, No. 2, pp. 309-320, 2002.

Imura, A., et al., "The Human OX40/gp34 System Directly Mediates Adhesion of Activated T Cells to Vascular Endothelial Cells", J. Exp. Med, vol. 183, pp. 2185-2195, 1996.

Ito, T., et al., "TSLP-activated dendritic cells induce an inflammatory T helper type 2 cell response through OX40 ligand", J. Exp. Med, vol. 202, No. 9, pp. 1213-1223, 2005.

Jember, A.G.H., et al., "Development of Allergic Inflammation in a Murine Model of Asthma is Dependent on the Costimulatory Receptor OX40", J. Exp. Med., vol. 193, No. 3, pp. 387-392, 2001.

Jordan, W.J., et al., "Optimal analysis of composite cytokine responses during alloreactivity", J. Immunol. Methods, vol. 260, pp. 1-14, 2002.

Kashmiri, S.V.S., et al., "SDR grafting—a new approach to antibody humanization", Methods, vol. 36, pp. 25-34, 2005.

Kettleborough, C.A., et al., "Isolation of tumor cell-specific single-chain Fv from immunized mice using phage-antibody libraries and the reconstruction of whole antibodies from these antibody fragments", Eur. J. Immunol., vol. 24, No. 4, pp. 952-958, 1994.

Kohler, G. & Milstein, C., "Continuous cultures of fused cells secreting antibody of predefined specificity", Nature, vol. 256, pp. 495-497, 1975.

Kozbor, D., et al., "The production of monoclonal antibodies from human lymphocytes", Immunology Today, vol. 4, No. 3, pp. 72-79, 1983.

Ling, E.M., et al., Relation of CD4+CD25+ regulatory T-cell suppression of allergen-driven T-cell activation to atopic status and expression of allergic disease, Lancet, vol. 363, pp. 608-615, 2004.

Low, N. M., et al., "Mimicking somatic hypermutation: affinity maturation of antibodies displayed on bacteriophage using a bacterial mutator strain", J. Mol. Biol., vol. 260, pp. 359-368, 1996.

Lukacs, N. W., et al., "The Production of Chemotactic Cytokines an Allogeneic Response", Am. J. Pathology, vol. 143, No. 4, pp. 1179-1188, 1993.

Madden, T.L., et al., "Applications of Network Blast Server", Meth. Enzymol., vol. 266, pp. 131-141, 1996.

Malmstrom, V., et al., "CD134L Expression on Dendritic Cells in the Mesenteric Lymph Nodes Drives Colitis in T Cell-Restored SCID Mice", J. Immunol., vol. 166, pp. 6972-6981, 2001.

Marks, J.D., et al., "By-passing Immunization Human: Building High Affinity Human Antibodies by Chain Shuffling", Bio/Technology, vol. 10, pp. 779-783, 1992.

Nohara, C., et al., "Amelioration of Experimental Autoimmune Encephalomyelitis with Anti-OX40 Ligand in Migration, but not Development, of Pathogenic T Cells", J. Immunol., vol. 166, pp. 2108-2115, 2001.

O'Flaherty, E., et al., "Regulation of T-cell apoptosis: a mixed lymphocyte reaction model", Immunology, vol. 100, pp. 289-299, 2000.

Pakala, S.V., et al., "Prevention of diabetes in NOD mice at a late stage by targeting OX40/OX40 ligand interactions", Eur. J. Immunol., vol. 34, pp. 3039-3046, 2004.

Patschan, S.,et al., "CD134 expression on CD4+ T cells is associated with nephritis and disease activity in patients with systemic lupus erythematosus", Clin. Exp. Immunol., vol. 145, pp. 235-242, 2006.

Patten, P., et al., "Applications of DNA shuffling to pharmaceuticals and vaccines,", Curr. Opin. Biotechnol., vol. 8, No. 6, pp. 724-733, 1997.

Persic, L., et al., "An integrated vector system for the eukaryotic expression of antibodies or their fragments after selection from phage display libraries", Gene, vol. 187, No. 1, pp. 9-18, 1997.

Ravetch, J.V., et al., "Structure of the human immunoglobulin μ locus: Characterization of embryonic and rearranged J and D genes", Cell, vol. 27, pp. 583-591, 1981.

Rensing, S.A., et al., predicted protein, partial [*Physcomitrella patens* subsp. *patens*], GenBank Accession No. XP_001761998, , Jan. 29, 2009 [online], downloaded from http://www.ncbi.nim.nih.gov/protein/168018930 on Mar. 25, 2012.

Riechmann, L., et al., "Reshaping human antibodies for therapy", Nature, vol. 332, pp. 323-324, 1988.

Salek-Ardakani, S., et al., "OX40 (CD134) Controls Memory T Helper 2 Cells that Drive Lung Inflammation", J. Exp. Med., vol. 198, No. 2, pp. 315-324, 2003.

Seshasayee, D., et al., "In vivo blockade of OX40 ligand inhibits thymic stromal lymphopoietin driven atopic inflammation", J. Clin.. Invest., vol. 117, No. 12, pp. 3868-3878, 2007.

Sherman, L.A., et al., "The Molecular Basis of Allorecognition,", Annu. Rev. Immunol, vol. 11, pp. 385-402, 1993.

Souza, H.S., et al., "Expression of lymphocyte-endothelial receptor-ligand pairs, $\alpha 4\beta 7$/MAdCAM-1 and OX40/OX40 ligand in the colon and jejunum of patients with inflammatory bowel disease", Gut, vol. 45, pp. 856-863, 1999.

Stuber, E., et al., "The T Cell-B Cell Interaction via OX40-OX40L Is Necessary for the T Cell-Dependent Humoral Immune Response", J. Exp. Med, vol. 183,pp. 979-989, 1996.

Stuber, E., et al., "The expression of OX40 in immunologically mediated diseases of the gastrointestinal tract (Celiac disease, Crohn's disease, ulcerative colitis)", Eur. J. Clin. Invest., vol. 30, pp. 594-599, 2000.

Taylor, L., et al., "Identification of a soluble OX40 isoform: development of a specific and quantitative immunoassay", J. Immujnol. Methods, vol. 255, Nos. 1-2, pp. 67-72, 2001.

Thompson, J., et al., "Affinity maturation of a high-affinity human monoclonal antibody against the third hypervariable loop of human immunodeficiency virus: use of phage display to improve affinity and broaden strain reactivity", J. Mol. Biol., vol. 256, No. 1, pp. 77-88, 1996.

Thorpe, P.E., et al., "The preparation and cytotoxic properties of antibody-toxin conjugates", Immunol. Rev., vol. 62, pp. 119-158, 1982.

Tillie-Leblond, I., et al., "Inflammatory events in severe acute asthma", Allergy, vol. 60, No. 1, pp. 23-29, 2005.

Totsuka, T., et al., "Therapeutic effect of anti-OX40L and anti-TNF-$\alpha$ MAbs in a murine model of chronic colitis", Am. J. Physiol. Gastrointest. Liver Physiol., vol. 284, pp. G595-G603, 2003.

Vaughan,T.J., et al., "Human antibodies by design", Nature Biotechnology, vol. 16, No. 6, pp. 535-539, 1998.

Verma, R., et al., "Antibody engineering: comparison of bacterial, yeast, insect and mammalian expression systems", Journal of Immunological Methods, vol. 216, Nos. 1-2, pp. 165-181, 1998.

Wang, Y. et al., "OX40-OX40L interactions: a promising therapeutic target for allergic diseases?", J. Clin. Invest, vol. 117, No. 12, pp. 3655-3657, 2007.

Yang, W.P., et al., "CDR walking mutagenesis for the affinity maturation of a potent human anti-HIV-1 antibody into the picomolar range", J. Mol. Biol., vol. 254, pp. 392-403, 1995.

Yoshioka, T., et al., "Contribution of OX40/OX40 ligand interaction to the pathogenesis of rheumatoid arthritis", Eur. J. Immunol., vol. 30, No. 10, pp. 2815-2823, 2000.

Zhang, J., et al., "PowerBLAST: a new network Blast application for interactive or automated sequence analysis and annotation", Genome Res., vol. 7, No. 6, pp. 649-656, 1997.

International Search Report of International Application No. PCT/US2010/024377 mailed Apr. 25, 2012.

Ming Li et al., "Effects of CD134 Monoclonal Antibody on Hemolysis Activities and Expression of Perforin in Peripheral Blood Mononuclear Cells of Systemic Lupus Erythematosus Patients", Hybridoma, Aug. 1, 2007, pp. 191-200, vol. 26, No. 4.

Suchard et al, "Co-stimulatory molecules as therpeutic targets in allergic airways disease", Drug Discovery today: Therapeutic Strategies, Dec. 1, 2007, pp. 39-47, vol. 4, No. 1, Amsterdam, NL.

(56) References Cited

OTHER PUBLICATIONS

Van Wanrooij, E. J.A., et al., "Interruption of the Tnfrsf4/Tnfsf4 (OX40/OX40) Pathway Attenuates Atherogenesis in Low-Density Lipoprotein Receptor-Deficient Mice", Arteriosclerosis, Thrombosis, and Vascular Biology, Jan. 1, 2007, pp. 204-210, vol. 27, No. 1.

Weinberg, A.D., et al., "Selective depletion of myelin-reative T-cells with the anti OX40 antibody ameliorates autoimmune encephalomyelitis", Nature Medicine, Feb. 1, 1996, pp. 183-189, vol. 2, No. 2.

Weinberg, A. D., "Antibodies to OX—40 (CD134) can identify and eliminate autoreactive T cells: implications for human autoimmune disease", Molecular Medicine Today, Feb. 1, 1998, pp. 76-83, vol. 4, No. 2, Cambridge, GB.

Weinberg, A. D., "OX40: targeted immunotherapy—implications for tempering autoimmunity and enhancing vaccines", Trends in Immunology, Feb. 1, 2002, pp. 102-109, vol. 23, No. 2.

* cited by examiner

Figure 1

(a) Light Chain variable region of antibody A26 (SEQ ID NO:7)

DIQMTQSPSSLSASVGDRVTITCRATQSIYNALAWYQQKPGKAPKLLIYNANTLHTGVPSRF
SASGSGTDSTLTISSLQPEDFATYYCQQYYDYPLTFGGGTKVEIKR (b) Heavy chain variable region of antibody A26 (SEQ ID NO:9)

EVQLVESGGGLVQPGGSLRLSCAASGFTFTNYGIHWIRQAPGKGLEWVASISPSGGLTYYRD
SVKGRFTISRDDAKNSPYLQMNSLRAEDTAVYYCATGGEGIFDYWGQGTLVTVSS (c)

| | |
|---|---|
| CDRH1: | NYGIH (SEQ ID NO:1) |
| CDRH2: | SISPSGGLTYYRDSVKG (SEQ ID NO:2) |
| | SISPSGGLTYYRDSVEG (SEQ ID NO:20) |
| CDRH3: | GGEGIFDY (SEQ ID NO:3) |
| CDRL1: | RATQSIYNALA (SEQ ID NO:4) |
| | RATEDIYNALA (SEQ ID NO:21) |
| CDRL2: | NANTLHT (SEQ ID NO:5) |
| CDRL3: | QQYYDYPLT (SEQ ID NO:6) |

(d) Light chain of antibody A26 (SEQ ID NO:11)

DIQMTQSPSSLSASVGDRVTITCRATQSIYNALAWYQQKPGKAPKLLIYNANTLHTGVPSRF
SASGSGTDSTLTISSLQPEDFATYYCQQYYDYPLTFGGGTKVEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (e) Light chain of antibody A26 including signal sequence (SEQ ID NO:12)

MKKTAIAIAVALAGFATVAQADIQMTQSPSSLSASVGDRVTITCRATQSIYNALAWYQQKPG
KAPKLLIYNANTLHTGVPSRFSASGSGTDSTLTISSLQPEDFATYYCQQYYDYPLTFGGGTK
VEIKRTVAAPSVFIFPPSDEQLKSGTASVVCLLNNFYPREAKVQWKVDNALQSGNSQESVTE
QDSKDSTYSLSSTLTLSKADYEKHKVYACEVTHQGLSSPVTKSFNRGEC

Figure 1 continued (f) Heavy chain of antibody A26 (SEQ ID NO:15)

EVQLVESGGGLVQPGGSLRLSCAASGFTFTNYGIHWIRQAPGKGLEWVASISPSGGLTYYRD
SVKGRFTISRDDAKNSPYLQMNSLRAEDTAVYYCATGGEGIFDYWGQGTLVTVSSASTKGPS
VFPLAPSSKSTSGGTAALGCLVKDYFPEPVTVSWNSGALTSGVHTFPAVLQSSGLYSLSSVV
TVPSSSLGTQTYICNVNHKPSNTKVDKKVEPKSCDKTHTCAA (g) Heavy chain of antibody A26 including signal sequence (SEQ ID NO:16)

MKKTAIAIAVALAGFATVAQAEVQLVESGGGLVQPGGSLRLSCAASGFTFTNYGIHWIRQAP
GKGLEWVASISPSGGLTYYRDSVKGRFTISRDDAKNSPYLQMNSLRAEDTAVYYCATGGEGI
FDYWGQGTLVTVSSASTKGPSVFPLAPSSKSTSGGTAALGCLVKDYFPEPVTVSWNSGALTS
GVHTFPAVLQSSGLYSLSSVVTVPSSSLGTQTYICNVNHKPSNTKVDKKVEPKSCDKTHTCA
A (h) DNA encoding Light chain variable region of antibody A26 (SEQ ID NO:8)
GATATCCAGATGACCCAGAGTCCAAGCAGTCTCTCCGCCAGCGTAGGCGATCGTGTGACTATTACCTG
TCGTGCAACCCAGAGCATCTACAACGCTCTGGCTTGGTATCAGCAGAAACCGGGTAAAGCGCCAAAAC
TCCTGATCTACAACGCGAACACTCTGCATACCGGTGTTCCGTCTCGTTTCTCTGCGTCTGGTTCTGGT
ACGGACTCTACTCTGACCATCTCCTCTCTGCAGCCGGAAGATTTCGCGACCTACTACTGCCAGCAGTA
CTACGATTACCCACTGACGTTTGGTGGTGGTACCAAAGTTGAGATCAAACGT

Figure 1 continued (i) DNA encoding Heavy chain variable region of antibody A26 (SEQ ID NO:10)

GAGGTTCAGCTGGTCGAGTCTGGAGGCGGGCTTGTCCAGCCTGGAGGGAGCCTGCGTCTCTC
TTGTGCAGCAAGCGGTTTCACGTTCACCAACTACGGTATCCACTGGATTCGTCAGGCACCAG
GTAAAGGTCTGGAATGGGTAGCCTCTATCTCTCCGTCTGGTGGTCTGACGTACTACCGTGAC
TCTGTCAAAGGTCGTTTCACCATCTCTCGTGATGACGCGAAAAACTCTCCGTACCTGCAGAT
GAACTCTCTGCGTGCAGAAGATACCGCAGTGTACTACTGCGCTACTGGTGGTGAAGGTATCT
TCGACTACTGGGGTCAGGGTACCCTGGTAACTGTCTCGAGC (j) DNA encoding Light chain of antibody A26 (SEQ ID NO:13)

GATATCCAGATGACCCAGAGTCCAAGCAGTCTCTCCGCCAGCGTAGGCGATCGTGTGACTAT
TACCTGTCGTGCAACCCAGAGCATCTACAACGCTCTGGCTTGGTATCAGCAGAAACCGGGTA
AAGCGCCAAAACTCCTGATCTACAACGCGAACACTCTGCATACCGGTGTTCCGTCTCGTTTC
TCTGCGTCTGGTTCTGGTACGGACTCTACTCTGACCATCTCCTCTCTGCAGCCGGAAGATTT
CGCGACCTACTACTGCCAGCAGTACTACGATTACCCACTGACGTTTGGTGGTGGTACCAAAG
TTGAGATCAAACGTACGGTTGCAGCTCCATCCGTCTTCATCTTTCCACCGTCTGACGAACAG
CTCAAATCTGGTACTGCTTCTGTCGTTTGCCTCCTGAACAACTTCTATCCGCGTGAAGCGAA
AGTCCAGTGGAAAGTCGACAACGCACTCCAGTCTGGTAACTCTCAGGAATCTGTGACCGAAC
AGGACTCCAAAGACTCCACCTACTCTCTGTCTAGCACCCTGACTCTGTCCAAAGCAGACTAC
GAGAAACACAAAGTGTACGCTTGCGAAGTTACCCATCAGGGTCTGTCTTCTCCGGTTACCAA
AAGCTTTAATAGAGGGGAGTGTTAA (k) DNA encoding Light chain of antibody A26 including signal sequence (SEQ ID NO:14)

ATGAAAAAGACAGCTATCGCAATTGCAGTGGCCTTGGCTGGTTTCGCTACCGTAGCGCAAGC
TGATATCCAGATGACCCAGAGTCCAAGCAGTCTCTCCGCCAGCGTAGGCGATCGTGTGACTA
TTACCTGTCGTGCAACCCAGAGCATCTACAACGCTCTGGCTTGGTATCAGCAGAAACCGGGT
AAAGCGCCAAAACTCCTGATCTACAACGCGAACACTCTGCATACCGGTGTTCCGTCTCGTTT
CTCTGCGTCTGGTTCTGGTACGGACTCTACTCTGACCATCTCCTCTCTGCAGCCGGAAGATT
TCGCGACCTACTACTGCCAGCAGTACTACGATTACCCACTGACGTTTGGTGGTGGTACCAAA
GTTGAGATCAAACGTACGGTTGCAGCTCCATCCGTCTTCATCTTTCCACCGTCTGACGAACA
GCTCAAATCTGGTACTGCTTCTGTCGTTTGCCTCCTGAACAACTTCTATCCGCGTGAAGCGA
AAGTCCAGTGGAAAGTCGACAACGCACTCCAGTCTGGTAACTCTCAGGAATCTGTGACCGAA
CAGGACTCCAAAGACTCCACCTACTCTCTGTCTAGCACCCTGACTCTGTCCAAAGCAGACTA
CGAGAAACACAAAGTGTACGCTTGCGAAGTTACCCATCAGGGTCTGTCTTCTCCGGTTACCA
AAAGCTTTAATAGAGGGGAGTGTTAA

Figure 1 continued (l) DNA encoding Heavy chain of antibody A26 (SEQ ID NO:17)

GAGGTTCAGCTGGTCGAGTCTGGAGGCGGGCTTGTCCAGCCTGGAGGGAGCCTGCGTCTCTC
TTGTGCAGCAAGCGGTTTCACGTTCACCAACTACGGTATCCACTGGATTCGTCAGGCACCAG
GTAAAGGTCTGGAATGGGTAGCCTCTATCTCTCCGTCTGGTGGTCTGACGTACTACCGTGAC
TCTGTCAAAGGTCGTTTCACCATCTCTCGTGATGACGCGAAAAACTCTCCGTACCTGCAGAT
GAACTCTCTGCGTGCAGAAGATACCGCAGTGTACTACTGCGCTACTGGTGGTGAAGGTATCT
TCGACTACTGGGGTCAGGGTACCCTGGTAACTGTCTCGAGCGCTTCTACCAAAGGTCCGAGC
GTTTTCCCACTGGCTCCGAGCTCTAAATCCACCTCTGGTGGTACGGCTGCACTGGGTTGCCT
GGTGAAAGACTACTTCCCAGAACCAGTTACCGTGTCTTGGAACTCTGGTGCACTGACCTCTG
GTGTTCACACCTTTCCAGCAGTTCTGCAGTCTTCTGGTCTGTACTCCCTGTCTAGCGTGGTT
ACCGTTCCGTCTTCTTCTCTGGGTACTCAGACCTACATCTGCAACGTCAACCACAAACCGTC
CAACACGAAAGTGGACAAAAAAGTCGAGCCGAAATCCTGTGACAAAACCCATACCTGCGCTG
CGTAA (m) DNA encoding Heavy chain of antibody A26 including signal sequence (SEQ ID NO:18)

ATGAAGAAGACTGCTATAGCAATTGCAGTGGCGCTAGCTGGTTTCGCCACCGTGGCGCAAGC
TGAGGTTCAGCTGGTCGAGTCTGGAGGCGGGCTTGTCCAGCCTGGAGGGAGCCTGCGTCTCT
CTTGTGCAGCAAGCGGTTTCACGTTCACCAACTACGGTATCCACTGGATTCGTCAGGCACCA
GGTAAAGGTCTGGAATGGGTAGCCTCTATCTCTCCGTCTGGTGGTCTGACGTACTACCGTGA
CTCTGTCAAAGGTCGTTTCACCATCTCTCGTGATGACGCGAAAAACTCTCCGTACCTGCAGA
TGAACTCTCTGCGTGCAGAAGATACCGCAGTGTACTACTGCGCTACTGGTGGTGAAGGTATC
TTCGACTACTGGGGTCAGGGTACCCTGGTAACTGTCTCGAGCGCTTCTACCAAAGGTCCGAG
CGTTTTCCCACTGGCTCCGAGCTCTAAATCCACCTCTGGTGGTACGGCTGCACTGGGTTGCC
TGGTGAAAGACTACTTCCCAGAACCAGTTACCGTGTCTTGGAACTCTGGTGCACTGACCTCT
GGTGTTCACACCTTTCCAGCAGTTCTGCAGTCTTCTGGTCTGTACTCCCTGTCTAGCGTGGT
TACCGTTCCGTCTTCTTCTCTGGGTACTCAGACCTACATCTGCAACGTCAACCACAAACCGT
CCAACACGAAAGTGGACAAAAAAGTCGAGCCGAAATCCTGTGACAAAACCCATACCTGCGCT
GCGTAA

Figure 1 continued (n) DNA encoding heavy and light chain of antibody A26 including intergenic sequence IGS2 (SEQ ID NO:19)

ATGAAAAAGACAGCTATCGCAATTGCAGTGGCCTTGGCTGGTTTCGCTACCGTAGCGCAAGC
TGATATCCAGATGACCCAGAGTCCAAGCAGTCTCTCCGCCAGCGTAGGCGATCGTGTGACTA
TTACCTGTCGTGCAACCCAGAGCATCTACAACGCTCTGGCTTGGTATCAGCAGAAACCGGGT
AAAGCGCCAAAACTCCTGATCTACAACGCGAACACTCTGCATACCGGTGTTCCGTCTCGTTT
CTCTGCGTCTGGTTCTGGTACGGACTCTACTCTGACCATCTCCTCTCTGCAGCCGGAAGATT
TCGCGACCTACTACTGCCAGCAGTACTACGATTACCCACTGACGTTTGGTGGTGGTACCAAA
GTTGAGATCAAACGTACGGTTGCAGCTCCATCCGTCTTCATCTTTCCACCGTCTGACGAACA
GCTCAAATCTGGTACTGCTTCTGTCGTTTGCCTCCTGAACAACTTCTATCCGCGTGAAGCGA
AAGTCCAGTGGAAAGTCGACAACGCACTCCAGTCTGGTAACTCTCAGGAATCTGTGACCGAA
CAGGACTCCAAAGACTCCACCTACTCTCTGTCTAGCACCCTGACTCTGTCCAAAGCAGACTA
CGAGAAACACAAAGTGTACGCTTGCGAAGTTACCCATCAGGGTCTGTCTTCTCCGGTTACCA
AAAGCTTTAATAGAGGGGAGTGTTAAAATGAAGAAGACTGCTATAGCAATTGCAGTGGCGCT
AGCTGGTTTCGCCACCGTGGCGCAAGCTGAGGTTCAGCTGGTCGAGTCTGGAGGCGGGCTTG
TCCAGCCTGGAGGGAGCCTGCGTCTCTCTTGTGCAGCAAGCGGTTTCACGTTCACCAACTAC
GGTATCCACTGGATTCGTCAGGCACCAGGTAAAGGTCTGGAATGGGTAGCCTCTATCTCTCC
GTCTGGTGGTCTGACGTACTACCGTGACTCTGTCAAAGGTCGTTTCACCATCTCTCGTGATG
ACGCGAAAAACTCTCCGTACCTGCAGATGAACTCTCTGCGTGCAGAAGATACCGCAGTGTAC
TACTGCGCTACTGGTGGTGAAGGTATCTTCGACTACTGGGGTCAGGGTACCCTGGTAACTGT
CTCGAGCGCTTCTACCAAAGGTCCGAGCGTTTTCCCACTGGCTCCGAGCTCTAAATCCACCT
CTGGTGGTACGGCTGCACTGGGTTGCCTGGTGAAAGACTACTTCCCAGAACCAGTTACCGTG
TCTTGGAACTCTGGTGCACTGACCTCTGGTGTTCACACCTTTCCAGCAGTTCTGCAGTCTTC
TGGTCTGTACTCCCTGTCTAGCGTGGTTACCGTTCCGTCTTCTTCTCTGGGTACTCAGACCT
ACATCTGCAACGTCAACCACAAACCGTCCAACACGAAAGTGGACAAAAAGTCGAGCCGAAA
TCCTGTGACAAAACCCATACCTGCGCTGCGTAA

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial
<220> FEATURE:
<223> OTHER INFORMATION: CDRH1

<400> SEQUENCE: 1

Asn Tyr Gly Ile His
1               5

<210> SEQ ID NO 2
<211> LENGTH: 17
<212> TYPE: PRT
<213> ORGANISM: Artificial
<220> FEATURE:
<223> OTHER INFORMATION: CDRH2

<400> SEQUENCE: 2

Ser Ile Ser Pro Ser Gly Gly Leu Thr Tyr Tyr Arg Asp Ser Val Lys
```

```
                1               5                  10                 15
Gly

<210> SEQ ID NO 3
<211> LENGTH: 8
<212> TYPE: PRT
<213> ORGANISM: Artificial
<220> FEATURE:
<223> OTHER INFORMATION: CDRH3

<400> SEQUENCE: 3

Gly Gly Glu Gly Ile Phe Asp Tyr
1               5

<210> SEQ ID NO 4
<211> LENGTH: 11
<212> TYPE: PRT
<213> ORGANISM: Artificial
<220> FEATURE:
<223> OTHER INFORMATION: CDRL1

<400> SEQUENCE: 4

Arg Ala Thr Gln Ser Ile Tyr Asn Ala Leu Ala
1               5                   10

<210> SEQ ID NO 5
<211> LENGTH: 7
<212> TYPE: PRT
<213> ORGANISM: Artificial
<220> FEATURE:
<223> OTHER INFORMATION: CDRL2

<400> SEQUENCE: 5

Asn Ala Asn Thr Leu His Thr
1               5

<210> SEQ ID NO 6
<211> LENGTH: 9
<212> TYPE: PRT
<213> ORGANISM: Artificial
<220> FEATURE:
<223> OTHER INFORMATION: CDRL3

<400> SEQUENCE: 6

Gln Gln Tyr Tyr Asp Tyr Pro Leu Thr
1               5

<210> SEQ ID NO 7
<211> LENGTH: 108
<212> TYPE: PRT
<213> ORGANISM: Artificial
<220> FEATURE:
<223> OTHER INFORMATION: Light Chain variable region of antibody A26

<400> SEQUENCE: 7

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
                20                  25                  30

Leu Ala Trp Tyr Gln Gln Lys Pro Gly Lys Ala Pro Lys Leu Leu Ile
            35                  40                  45

Tyr Asn Ala Asn Thr Leu His Thr Gly Val Pro Ser Arg Phe Ser Ala
        50                  55                  60

Ser Gly Ser Gly Thr Asp Ser Leu Thr Ile Ser Ser Leu Gln Pro
65                  70                  75                  80
```

```
Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg
            100                 105

<210> SEQ ID NO 8
<211> LENGTH: 324
<212> TYPE: DNA
<213> ORGANISM: Artificial
<220> FEATURE:
<223> OTHER INFORMATION: DNA encoding Light chain variable region of
      antibody A26

<400> SEQUENCE: 8
gatatccaga tgacccagag tccaagcagt ctctccgcca gcgtaggcga tcgtgtgact      60
attacctgtc gtgcaaccca gagcatctac aacgctctgg cttggtatca gcagaaaccg     120
ggtaaagcgc aaaaactcct gatctacaac gcgaacactc tgcataccgg tgttccgtct     180
cgtttctctg cgtctggttc tggtacggac tctactctga ccatctcctc tctgcagccg     240
gaagatttcg cgacctacta ctgccagcag tactacgatt acccactgac gtttggtggt     300
ggtaccaaag ttgagatcaa acgt                                            324

<210> SEQ ID NO 9
<211> LENGTH: 117
<212> TYPE: PRT
<213> ORGANISM: Artificial
<220> FEATURE:
<223> OTHER INFORMATION: Heavy chain variable region of antibody A26

<400> SEQUENCE: 9

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser
        115

<210> SEQ ID NO 10
<211> LENGTH: 351
<212> TYPE: DNA
<213> ORGANISM: Artificial
<220> FEATURE:
<223> OTHER INFORMATION: DNA encoding Heavy chain variable region of
      antibody A26

<400> SEQUENCE: 10
gaggttcagc tggtcgagtc tggaggcggg cttgtccagc ctggaggag cctgcgtctc       60 tcttgtgcag caagcggttt cacgttcacc aactacggta tccactggat tcgtcaggca     120
ccaggtaaag gtctggaatg ggtagcctct atctctccgt ctggtggtct gacgtactac     180
```

```
cgtgactctg tcaaaggtcg tttcaccatc tctcgtgatg acgcgaaaaa ctctccgtac    240
ctgcagatga actctctgcg tgcagaagat accgcagtgt actactgcgc tactggtggt    300
gaaggtatct tcgactactg gggtcagggt accctggtaa ctgtctcgag c             351
```

```
<210> SEQ ID NO 11
<211> LENGTH: 214
<212> TYPE: PRT
<213> ORGANISM: Artificial
<220> FEATURE:
<223> OTHER INFORMATION: Light chain of antibody A26

<400> SEQUENCE: 11

Asp Ile Gln Met Thr Gln Ser Pro Ser Ser Leu Ser Ala Ser Val Gly
1               5                   10                  15

Asp Arg Val Thr Ile Thr Cys Arg Ala Thr Gln Ser Ile Tyr Asn Ala
            20                  25                  30

Leu Ala Trp Tyr Gln Gln Lys Pro Gly Lys Ala Pro Lys Leu Leu Ile
        35                  40                  45

Tyr Asn Ala Asn Thr Leu His Thr Gly Val Pro Ser Arg Phe Ser Ala
50                  55                  60

Ser Gly Ser Gly Thr Asp Ser Thr Leu Thr Ile Ser Ser Leu Gln Pro
65                  70                  75                  80

Glu Asp Phe Ala Thr Tyr Tyr Cys Gln Gln Tyr Tyr Asp Tyr Pro Leu
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 12
<211> LENGTH: 235
<212> TYPE: PRT
<213> ORGANISM: Artificial
<220> FEATURE:
<223> OTHER INFORMATION: Light chain of antibody A26 including signal
      sequence

<400> SEQUENCE: 12

Met Lys Lys Thr Ala Ile Ala Ile Ala Val Ala Leu Ala Gly Phe Ala
1               5                   10                  15

Thr Val Ala Gln Ala Asp Ile Gln Met Thr Gln Ser Pro Ser Ser Leu
            20                  25                  30

Ser Ala Ser Val Gly Asp Arg Val Thr Ile Thr Cys Arg Ala Thr Gln
        35                  40                  45

Ser Ile Tyr Asn Ala Leu Ala Trp Tyr Gln Gln Lys Pro Gly Lys Ala
```

```
                50                  55                  60
Pro Lys Leu Leu Ile Tyr Asn Ala Asn Thr Leu His Thr Gly Val Pro
65                  70                  75                  80

Ser Arg Phe Ser Ala Ser Gly Ser Gly Thr Asp Ser Thr Leu Thr Ile
                85                  90                  95

Ser Ser Leu Gln Pro Glu Asp Phe Ala Thr Tyr Tyr Cys Gln Gln Tyr
            100                 105                 110

Tyr Asp Tyr Pro Leu Thr Phe Gly Gly Gly Thr Lys Val Glu Ile Lys
        115                 120                 125

Arg Thr Val Ala Ala Pro Ser Val Phe Ile Phe Pro Pro Ser Asp Glu
    130                 135                 140

Gln Leu Lys Ser Gly Thr Ala Ser Val Val Cys Leu Leu Asn Asn Phe
145                 150                 155                 160

Tyr Pro Arg Glu Ala Lys Val Gln Trp Lys Val Asp Asn Ala Leu Gln
                165                 170                 175

Ser Gly Asn Ser Gln Glu Ser Val Thr Glu Gln Asp Ser Lys Asp Ser
            180                 185                 190

Thr Tyr Ser Leu Ser Ser Thr Leu Thr Leu Ser Lys Ala Asp Tyr Glu
        195                 200                 205

Lys His Lys Val Tyr Ala Cys Glu Val Thr His Gln Gly Leu Ser Ser
    210                 215                 220

Pro Val Thr Lys Ser Phe Asn Arg Gly Glu Cys
225                 230                 235

<210> SEQ ID NO 13
<211> LENGTH: 645
<212> TYPE: DNA
<213> ORGANISM: Artificial
<220> FEATURE:
<223> OTHER INFORMATION: DNA encoding Light chain of antibody A26

<400> SEQUENCE: 13
gatatccaga tgacccagag tccaagcagt ctctccgcca gcgtaggcga tcgtgtgact      60
attacctgtc gtgcaaccca gagcatctac aacgctctgg cttggtatca gcagaaaccg     120
ggtaaagcgc caaaactcct gatctacaac gcgaacactc tgcataccgg tgttccgtct     180
cgtttctctg cgtctggttc tggtacggac tctactctga ccatctcctc tctgcagccg     240
gaagatttcg cgacctacta ctgccagcag tactacgatt acccactgac gtttggtggt     300
ggtaccaaag ttgagatcaa acgtacggtt gcagctccat ccgtcttcat ctttccaccg     360
tctgacgaac agctcaaatc tggtactgct tctgtcgttt gcctcctgaa caacttctat     420
ccgcgtgaag cgaaagtcca gtggaaagtc gacaacgcac tccagtctgg taactctcag     480
gaatctgtga ccgaacagga ctccaaagac tccacctact ctctgtctag cacccctgact    540 ctgtccaaag cagactacga aaacacaaa gtgtacgctt gcgaagttac ccatcagggt     600
ctgtcttctc cggttaccaa aagctttaat agaggggagt gttaa                    645

<210> SEQ ID NO 14
<211> LENGTH: 708
<212> TYPE: DNA
<213> ORGANISM: Artificial
<220> FEATURE:
<223> OTHER INFORMATION: DNA encoding Light chain of antibody A26
      including signal sequence

<400> SEQUENCE: 14
atgaaaaaga cagctatcgc aattgcagtg gccttggctg gtttcgctac cgtagcgcaa      60
```

```
gctgatatcc agatgaccca gagtccaagc agtctctccg ccagcgtagg cgatcgtgtg    120
actattacct gtcgtgcaac ccagagcatc tacaacgctc tggcttggta tcagcagaaa    180
ccgggtaaag cgccaaaact cctgatctac aacgcgaaca ctctgcatac cggtgttccg    240
tctcgtttct ctgcgtctgg ttctggtacg gactctactc tgaccatctc ctctctgcag    300
ccggaagatt tcgcgaccta ctactgccag cagtactacg attacccact gacgtttggt    360
ggtggtacca agttgagat caaacgtacg gttgcagctc catccgtctt catctttcca    420
ccgtctgacg aacagctcaa atctggtact gcttctgtcg tttgcctcct gaacaacttc    480
tatccgcgtg aagcgaaagt ccagtggaaa gtcgacaacg cactccagtc tggtaactct    540
caggaatctg tgaccgaaca ggactccaaa gactccacct actctctgtc tagcaccctg    600
actctgtcca aagcagacta cgagaaacac aaagtgtacg cttgcgaagt tacccatcag    660
ggtctgtctt ctccggttac caaaagcttt aatagagggg agtgttaa                 708
```

```
<210> SEQ ID NO 15
<211> LENGTH: 228
<212> TYPE: PRT
<213> ORGANISM: Artificial
<220> FEATURE:
<223> OTHER INFORMATION: Heavy chain of antibody A26

<400> SEQUENCE: 15
```

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Tyr
            20                  25                  30

Gly Ile His Trp Ile Arg Gln Ala Pro Gly Lys Gly Leu Glu Trp Val
        35                  40                  45

Ala Ser Ile Ser Pro Ser Gly Gly Leu Thr Tyr Tyr Arg Asp Ser Val
    50                  55                  60

Lys Gly Arg Phe Thr Ile Ser Arg Asp Asp Ala Lys Asn Ser Pro Tyr
65                  70                  75                  80

Leu Gln Met Asn Ser Leu Arg Ala Glu Asp Thr Ala Val Tyr Tyr Cys
                85                  90                  95

Ala Thr Gly Gly Glu Gly Ile Phe Asp Tyr Trp Gly Gln Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Lys Val Glu Pro Lys Ser Cys Asp Lys Thr His
    210                 215                 220

Thr Cys Ala Ala
225
```

```
<210> SEQ ID NO 16
<211> LENGTH: 248
```

<212> TYPE: PRT
<213> ORGANISM: Artificial
<220> FEATURE:
<223> OTHER INFORMATION: Heavy chain of antibody A26 including signal
      sequence

<400> SEQUENCE: 16

Met Lys Lys Thr Ala Ile Ala Ile Ala Val Ala Leu Ala Gly Phe Ala
1               5                   10                  15

Thr Val Ala Gln Ala Glu Val Gln Leu Val Glu Ser Gly Gly Gly Leu
            20                  25                  30

Val Gln Pro Gly Gly Ser Leu Arg Leu Ser Cys Ala Ala Ser Gly Phe
        35                  40                  45

Thr Phe Thr Asn Tyr Gly Ile His Trp Ile Arg Gln Ala Pro Gly Lys
    50                  55                  60

Gly Leu Glu Trp Val Ala Ser Ile Ser Pro Ser Gly Gly Leu Thr Tyr
65                  70                  75                  80

Tyr Arg Asp Ser Val Lys Gly Arg Phe Thr Ile Ser Arg Asp Asp Ala
                85                  90                  95

Lys Asn Ser Pro Tyr Leu Gln Met Asn Ser Leu Arg Ala Glu Asp Thr
            100                 105                 110

Ala Val Tyr Tyr Cys Ala Thr Gly Gly Glu Gly Ile Phe Asp Tyr Trp
        115                 120                 125

Gly Gln Gly Thr Leu Val Thr Val Ser Ser Ala Ser Thr Lys Gly Pro
    130                 135                 140

Ser Val Phe Pro Leu Ala Pro Ser Ser Lys Ser Thr Ser Gly Gly Thr
145                 150                 155                 160

Ala Ala Leu Gly Cys Leu Val Lys Asp Tyr Phe Pro Glu Pro Val Thr
                165                 170                 175

Val Ser Trp Asn Ser Gly Ala Leu Thr Ser Gly Val His Thr Phe Pro
            180                 185                 190

Ala Val Leu Gln Ser Ser Gly Leu Tyr Ser Leu Ser Ser Val Val Thr
        195                 200                 205

Val Pro Ser Ser Ser Leu Gly Thr Gln Thr Tyr Ile Cys Asn Val Asn
    210                 215                 220

His Lys Pro Ser Asn Thr Lys Val Asp Lys Val Glu Pro Lys Ser
225                 230                 235                 240

Cys Asp Lys Thr His Thr Cys Ala
                245

<210> SEQ ID NO 17
<211> LENGTH: 687
<212> TYPE: DNA
<213> ORGANISM: Artificial
<220> FEATURE:
<223> OTHER INFORMATION: DNA encoding Heavy chain of antibody A26

<400> SEQUENCE: 17
gaggttcagc tggtcgagtc tggaggcggg cttgtccagc ctggagggag cctgcgtctc      60
tcttgtgcag caagcggttt cacgttcacc aactacggta tccactggat tcgtcaggca     120
ccaggtaaag gtctggaatg gtagcctct atctctccgt ctggtggtct gacgtactac      180
cgtgactctg tcaaaggtcg tttcaccatc tctcgtgatg acgcgaaaaa ctctccgtac     240
ctgcagatga actctctgcg tgcagaagat accgcagtgt actactgcgc tactggtggt     300
gaaggtatct cgactactg ggtcagggt accctggtaa ctgtctcgag cgcttctacc       360
aaaggtccga gcgttttccc actggctccg agctctaaat ccacctctgg tggtacggct     420

```
gcactgggtt gcctggtgaa agactacttc ccagaaccag ttaccgtgtc ttggaactct     480
ggtgcactga cctctggtgt tcacaccttt ccagcagttc tgcagtcttc tggtctgtac     540
tccctgtcta gcgtggttac cgttccgtct tcttctctgg gtactcagac ctacatctgc     600
aacgtcaacc acaaaccgtc caacacgaaa gtggacaaaa agtcgagcc gaaatcctgt      660 gacaaaaccc atacctgcgc tgcgtaa                                         687
```

<210> SEQ ID NO 18
<211> LENGTH: 750
<212> TYPE: DNA
<213> ORGANISM: Artificial
<220> FEATURE:
<223> OTHER INFORMATION: DNA encoding Heavy chain of antibody A26
      including signal sequence

<400> SEQUENCE: 18

```
atgaagaaga ctgctatagc aattgcagtg gcgctagctg gtttcgccac cgtggcgcaa      60
gctgaggttc agctggtcga gtctggaggc gggcttgtcc agcctggagg gagcctgcgt     120
ctctcttgtg cagcaagcgg tttcacgttc accaactacg gtatccactg gattcgtcag     180
gcaccaggta aaggtctgga atgggtagcc tctatctctc cgtctggtgg tctgacgtac     240
taccgtgact ctgtcaaagg tcgtttcacc atctctcgtg atgacgcgaa aaactctccg     300
tacctgcaga tgaactctct gcgtgcagaa gataccgcag tgtactactg cgctactggt     360
ggtgaaggta tcttcgacta ctggggtcag ggtaccctgg taactgtctc gagcgcttct     420
accaaaggtc cgagcgtttt cccactggct ccgagctcta aatccacctc tggtggtacg     480
gctgcactgg gttgcctggt gaaagactac ttcccagaac cagttaccgt gtcttggaac     540
tctggtgcac tgacctctgg tgttcacacc tttccagcag ttctgcagtc ttctggtctg     600
tactccctgt ctagcgtggt taccgttccg tcttcttctc tgggtactca gacctacatc     660
tgcaacgtca accacaaacc gtccaacacg aaagtggaca aaaagtcga gccgaaatcc     720 tgtgacaaaa cccatacctg cgctgcgtaa                                      750
```

<210> SEQ ID NO 19
<211> LENGTH: 1459
<212> TYPE: DNA
<213> ORGANISM: Artificial
<220> FEATURE:
<223> OTHER INFORMATION: DNA encoding heavy and light chain of antibody
      A26 including intergenic sequence IGS2

<400> SEQUENCE: 19

```
atgaaaaaga cagctatcgc aattgcagtg gccttggctg gtttcgctac cgtagcgcaa      60
gctgatatcc agatgaccca gagtccaagc agtctctccg ccagcgtagg cgatcgtgtg     120
actattacct gtcgtgcaac ccagagcatc tacaacgctc tggcttggta tcagcagaaa     180
ccgggtaaag cgccaaaact cctgatctac aacgcgaaca ctctgcatac cggtgttccg     240 tctcgttttct ctgcgtctgg ttctggtacg gactctactc tgaccatctc ctctctgcag     300
ccggaagatt tcgcgaccta ctactgccag cagtactacg attacccact gacgtttggt     360
ggtggtacca agttgagat caaacgtacg gttgcagctc catccgtctt catctttcca     420
ccgtctgacg aacagctcaa atctggtact gcttctgtcg tttgcctcct gaacaacttc     480
tatccgcgtg aagcgaaagt ccagtggaaa gtcgacaacg cactccagtc tggtaactct     540
caggaatctg tgaccgaaca ggactccaaa gactccacct actctctgtc tagcaccctg     600
actctgtcca aagcagacta cgagaaacac aaagtgtacg cttgcgaagt tacccatcag     660
```

```
ggtctgtctt ctccggttac caaaagcttt aatagagggg agtgttaaaa tgaagaagac      720
tgctatagca attgcagtgg cgctagctgg tttcgccacc gtggcgcaag ctgaggttca      780
gctggtcgag tctggaggcg ggcttgtcca gcctggaggg agcctgcgtc tctcttgtgc      840
agcaagcggt ttcacgttca ccaactacgg tatccactgg attcgtcagg caccaggtaa      900
aggtctggaa tgggtagcct ctatctctcc gtctggtggt ctgacgtact accgtgactc      960
tgtcaaaggt cgtttcacca tctctcgtga tgacgcgaaa aactctccgt acctgcagat     1020
gaactctctg cgtgcagaag ataccgcagt gtactactgc gctactggtg gtgaaggtat     1080
cttcgactac tggggtcagg gtaccctggt aactgtctcg agcgcttcta ccaaaggtcc     1140
gagcgttttc ccactggctc cgagctctaa atccacctct ggtggtacgg ctgcactggg     1200
ttgcctggtg aaagactact ccccagaacc agttaccgtg tcttggaact ctggtgcact     1260
gacctctggt gttcacacct ttccagcagt tctgcagtct tctggtctgt actccctgtc     1320
tagcgtggtt accgttccgt cttcttctct gggtactcag acctacatct gcaacgtcaa     1380
ccacaaaccg tccaacacga agtggacaa aaaagtcgag ccgaaatcct gtgacaaaac     1440
ccatacctgc gctgcgtaa                                                  1459
```

<210> SEQ ID NO 20
<211> LENGTH: 17
<212> TYPE: PRT
<213> ORGANISM: Artificial
<220> FEATURE:
<223> OTHER INFORMATION: CDRH2

<400> SEQUENCE: 20

Ser Ile Ser Pro Ser Gly Gly Leu Thr Tyr Tyr Arg Asp Ser Val Glu
1               5                   10                  15
Gly

<210> SEQ ID NO 21
<211> LENGTH: 11
<212> TYPE: PRT
<213> ORGANISM: Artificial
<220> FEATURE:
<223> OTHER INFORMATION: CDRL1

<400> SEQUENCE: 21

Arg Ala Thr Glu Asp Ile Tyr Asn Ala Leu Ala
1               5                   10

<210> SEQ ID NO 22
<211> LENGTH: 11
<212> TYPE: PRT
<213> ORGANISM: Artificial
<220> FEATURE:
<223> OTHER INFORMATION: human JH4

<400> SEQUENCE: 22

Trp Gly Gln Gly Thr Leu Val Thr Val Ser Ser
1               5                   10

<210> SEQ ID NO 23
<211> LENGTH: 10
<212> TYPE: PRT
<213> ORGANISM: Artificial
<220> FEATURE:
<223> OTHER INFORMATION: JK1 sequence

```
<400> SEQUENCE: 23

Phe Gly Gln Gly Thr Lys Val Glu Ile Lys
1               5                   10
```

ANTIBODY MOLECULES HAVING SPECIFICITY FOR HUMAN OX40

CROSS-REFERENCE TO RELATED APPLICATIONS

This application claims priority to U.S. Application Ser. No. 61/153,038, filed on Feb. 17, 2009, which is incorporated by reference in its entirety.

The present invention relates to antibody molecules having specificity for antigenic determinants of OX40 and compositions comprising the same. The present invention also relates to the therapeutic uses of the antibody molecules, compositions and methods for producing said antibody molecules.

OX40 (also known as CD134, TNFRSF4, ACT35 or TXGP1L) is a member of the TNF receptor superfamily, which includes 4-1BB, CD27, CD30 and CD40. The extracellular ligand binding domain of OX40 is composed of 3 full cysteine-rich domains (CRDs) and a partial, fourth C-terminal CRD (Bodmer et al., 2002, Trends Biochem Sci, 27, 19-26).

The ligand for OX40 is OX40L and 3 copies of OX40 bind to the trimeric ligand to form the OX40-OX40L complex (Compaan and Hymowitz, 2006, Structure, 14, 1321-1330). OX40 is a membrane-bound receptor; however a soluble isoform has also been detected (Taylor and Schwarz, 2001, J. Immunol. Methods, 255, 67-72). The functional significance of the soluble form is presently unknown. OX40 is not expressed on resting T cells, but is transiently expressed on activated T cells after ligation of the T cell receptor (TCR). The ligand for OX40, OX40L, is a member of the TNF family and is expressed on activated antigen presenting cells (APC), including B cells, macrophages, endothelial cells and dendritic cells (DC).

OX40 is a major costimulatory receptor with sequential engagement of CD28 and OX40 being required for optimal T cell proliferation and survival. Ligation of OX40 on activated T cells leads to enhanced cytokine production and proliferation of both CD4+ and CD8+ T cells (Gramaglia et al., 2000, J. Immunol, 165, 3043-3050, Bansal-Pakala et al., 2004, J. Immunol, 172, 4821-425) and can contribute to both ongoing Th1 and Th2 responses (Gramaglia et al., 1998, J. Immuno., 161, 6510-6517, Arestides et al., 2002, Eur. J. Immunol. 32, 2874-2880). OX40 costimulation prolongs T cell survival beyond the initial effector phase of the immune response and increases the number of memory T cells through inhibition of effector T cell death.

When immune activation is excessive or uncontrolled, pathological allergy, asthma, inflammation, autoimmune and other related diseases may occur. Because OX40 functions to enhance immune responses, it may exacerbate autoimmune and inflammatory diseases.

The role of OX40/OX40L interactions in models of disease has been demonstrated in OX40 knockout mice. In experimental allergic encephalomyelitis (EAE), a model of multiple sclerosis, less severe clinical signs of disease and reduced inflammatory infiltrate within the CNS was noted in OX40 knockout mice (Carboni et al., 2003, J. Neuroimmunology, 145, 1-11). Also OX40 knockout mice primed and challenged with ovalbumin exhibit diminished lung inflammation (80-90% reduction in eosinophilia), reduced mucus production, and significantly attenuated airway hyper-reactivity (Jember et al., 2001, J. Exp. Med., 193, 387-392). Monoclonal antibodies to murine OX40 ligand have shown beneficial effects in the collagen-induced arthritis model of rheumatoid arthritis (Yoshioka et al., 2000, Eur. J. Immunol., 30, 2815-2823), EAE (Nohara et al., 2001, J. Immunol., 166, 2108-2115), non-obese diabetic (NOD) mice (Pakala et al., 2004, Eur. J. Immunol., 34, 3039-3046), colitis in T cell restored mice (Malmstrom et al., 2001, J. Immunol., 166, 6972-6981, Totsuka et al., 2003, Am. J. Physiol. Gastrointest. Liver Physiol., 284, G595-G603) and models of lung inflammation (Salek-Ardakani et al., 2003, J. Exp. Med., 198, 315-324, Hoshino et al., 2003, Eur. J. Immunol, 33, 861-869). An antibody to human OX40L has been profiled in a model of lung inflammation in rhesus monkeys and resulted in reduced levels of IL-5, IL-13 and effector memory T cells in bronchiolar lavage fluid after allergen challenge (Seshasayee et al., 2007, J. Clin. Invest, 117, 3868-3878).

An increase in the expression of OX40 has been noted in several autoimmune and inflammatory diseases. This includes an increase in OX40 expression on T cells isolated from the synovial fluid of rheumatoid arthritis patients (Brugnoni D et al., 1998, Br. J. Rheum., 37, 584-585; Yoshioka et al., 2000, Eur. J. Immunol., 30, 2815-2823; Giacomelli R et al., 2001, Clin. Exp. Rheumatol., 19, 317-320). Similarly an increase in OX40 expression has been noted in gastrointestinal tissue from patients with ulcerative colitis and Crohn's disease (Souza et al., 1999, Gut, 45, 856-863; Stuber et al., 2000, Eur. J. Clin. Invest., 30, 594-599) and in active lesions of patients with multiple sclerosis (Carboni et al., 2003, J. Neuroimmunology, 145, 1-11). OX40L can also be detected on human airway smooth muscle (ASM) and asthma patients ASM cells show greater inflammatory responses to OX40L ligation than healthy donors, indicating a role for the OX40/OX40L pathway in asthma (Burgess et al., 2004, J. Allergy Clin Immunol., 113, 683-689; Burgess et al., 2005, J. Allergy Clin Immunol., 115, 302-308). It has also been reported that CD4+ T cells isolated from the peripheral blood of systemic lupus erythematosus (SLE) patients express elevated levels of OX40 which is associated with disease activity (Patschan et al., 2006, Clin. Exp. Immunol., 145, 235-242).

Given the role of OX40 in allergy, asthma and diseases associated with autoimmunity and inflammation, one approach to therapy in these diseases is to block OX40-OX40L signalling through the use of anti-OX40L antibodies or antagonistic anti-OX40 antibodies Anti-OX40L antibodies have been described, see for example WO2006/029879. Numerous agonistic anti-OX40 antibodies have been described but very few antagonistic anti-OX40 antibodies are known. A rabbit polyclonal anti-mouse OX40 antibody was produced by Stuber et al., 1996, J. Exp. Med, 183, 979-989 which blocks the interaction between OX40 and OX40L. Mouse monoclonal antibodies, 131 and 315 which bind human OX40 were generated by Imura et al., 1996, J. Exp. Med, 2185-2195.

Fully human antagonistic antibodies have been described in WO2007/062245, the highest affinity of these antibodies had an affinity for cell surface expressed OX40 (activated T cells) of 11 nM.

Humanised antagonistic antibodies have been described in WO2008/106116 and the antibody with the best affinity for OX40 had an affinity of 0.94 nM.

Other anti-OX40 antibodies have been described, including murine L106 (U.S. Pat. No. 6,277,962) and murine ACT35, commercially available from eBioscience.

Accordingly there is still a need in the art for an improved anti-OX40 antibody suitable for treating patients.

We have now identified a high affinity antagonistic anti-OX40 antibody suitable for use in the treatment or prophylaxis of pathological disorders mediated by OX40 or associated with an increased level of OX40.

BRIEF DESCRIPTION OF THE DRAWINGS

FIG. 1 shows certain amino acid or DNA sequences relating to an antibody according to the disclosure

Humanised CA044_00026 generally in the form of a Fab fragment or other fragments, is referred to as A26.

Figure 2:
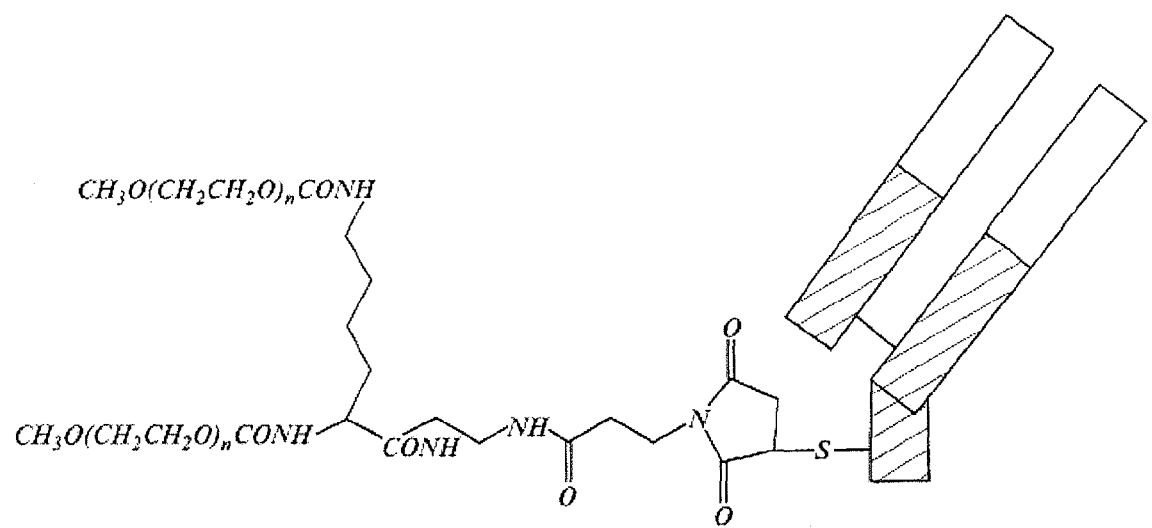
FIG. 2 shows a diagrammatic representation of an antibody of the A26 Fab'-PEG format

PEGylated antibody "A26" in the format shown in FIG. 2, is referred to herein as A26Fab'-PEG.

The residues in antibody variable domains are conventionally numbered according to a system devised by Kabat et al. This system is set forth in Kabat et al., 1987, in Sequences of Proteins of Immunological Interest, US Department of Health and Human Services, NIH, USA (hereafter "Kabat et al. (supra)"). This numbering system is used in the present specification except where otherwise indicated.

The Kabat residue designations do not always correspond directly with the linear numbering of the amino acid residues. The actual linear amino acid sequence may contain fewer or additional amino acids than in the strict Kabat numbering corresponding to a shortening of, or insertion into, a structural component, whether framework or complementarity determining region (CDR), of the basic variable domain structure. The correct Kabat numbering of residues may be determined for a given antibody by alignment of residues of homology in the sequence of the antibody with a "standard" Kabat numbered sequence.

The CDRs of the heavy chain variable domain are located at residues 31-35 (CDR-H1), residues 50-65 (CDR-H2) and residues 95-102 (CDR-H3) according to the Kabat numbering system. However, according to Chothia (Chothia, C. and Lesk, A. M. J. Mol. Biol., 196, 901-917 (1987)), the loop equivalent to CDR-H1 extends from residue 26 to residue 32. Thus unless indicated otherwise 'CDR-H1' as employed herein is intended to refer to residues 26 to 35, as described by a combination of the Kabat numbering system and Chothia's topological loop definition.

The CDRs of the light chain variable domain are located at residues 24-34 (CDR-L1), residues 50-56 (CDR-L2) and residues 89-97 (CDR-L3) according to the Kabat numbering system.

As used herein, the term 'antagonistic antibody' describes an antibody that is capable of inhibiting and/or neutralising the biological signalling activity of OX40, for example by blocking binding or substantially reducing binding of OX40 to OX40 ligand and thus inhibiting the activation of OX40.

Antibodies for use in the present invention may be obtained using any suitable method known in the art. The OX40 polypeptide/protein including fusion proteins, for example OX40-Fc fusions proteins or cells (recombinantly or naturally) expressing the polypeptide (such as activated T cells) can be used to produce antibodies which specifically recognise OX40. The OX40 polypeptide may be the 'mature' polypeptide or a biologically active fragment or derivative thereof. Suitably the OX40 polypeptide is the mature human polypeptide or the extracellular domain or fragment thereof. The extracellular domain typically comprises amino acids 29-214 of the OX40 protein (SWISS PROT entry P43489). OX40 polypeptides may be prepared by processes well known in the art from genetically engineered host cells comprising expression systems or they may be recovered from natural biological sources. In the present application, the term "polypeptides" includes peptides, polypeptides and proteins. These are used interchangeably unless otherwise specified. The OX40 polypeptide may in some instances be part of a larger protein such as a fusion protein for example fused to an affinity tag. Antibodies generated against the OX40 polypeptide may be obtained, where immunisation of an animal is necessary, by administering the polypeptides to an animal, preferably a non-human animal, using well-known and routine protocols, see for example Handbook of Experimental Immunology, D. M. Weir (ed.), Vol 4, Blackwell Scientific Publishers, Oxford, England, 1986). Many warm-blooded animals, such as rabbits, mice, rats, sheep, cows, camels or pigs may be immunized. However, mice, rabbits, pigs and rats are generally most suitable.

Antibodies for use in the present invention include whole antibodies and functionally active fragments or derivatives thereof and may be, but are not limited to, monoclonal, humanised, fully human or chimeric antibodies.

Monoclonal antibodies may be prepared by any method known in the art such as the hybridoma technique (Kohler & Milstein, 1975, Nature, 256:495-497), the trioma technique, the human B-cell hybridoma technique (Kozbor et al., 1983, Immunology Today, 4:72) and the EBV-hybridoma technique (Cole et al., Monoclonal Antibodies and Cancer Therapy, pp 77-96, Alan R Liss, Inc., 1985).

Antibodies for use in the invention may also be generated using single lymphocyte antibody methods by cloning and expressing immunoglobulin variable region cDNAs generated from single lymphocytes selected for the production of specific antibodies by, for example, the methods described by Babcook, J. et al., 1996, Proc. Natl. Acad. Sci. USA 93(15): 7843-78481; WO92/02551; WO2004/051268 and International Patent Application number WO2004/106377.

Screening for antibodies can be performed using assays to measure binding to human OX40 and/or assays to measure the ability to block the binding of OX40 to its ligand, OX40L. An example of a binding assay is an ELISA, in particular, using a fusion protein of human OX40 and human Fc, which is immobilized on plates, and employing a conjugated secondary antibody to detect anti-OX40 antibody bound to the fusion protein. An example of a blocking assay is a flow cytometry based assay measuring the blocking of OX40 ligand fusion protein binding to OX40 on human CD4 cells. A fluorescently labelled secondary antibody is used to detect the amount of OX40 ligand fusion protein binding to the cell. This assay is looking for a reduction in signal as the antibody in the supernatant blocks the binding of ligand fusion protein to OX40. A further example of a blocking assay is an assay where the blocking of costimulation of naive human T cells mediated by OX40 ligand fusion protein coated to a plate is measured by measuring tritiated thymidine incorporation.

Humanised antibodies (which include CDR-grafted antibodies) are antibody molecules having one or more complementarity determining regions (CDRs) from a non-human species and a framework region from a human immunoglobulin molecule (see, e.g. U.S. Pat. No. 5,585,089; WO91/09967). It will be appreciated that it may only be necessary to transfer the specificity determining residues of the CDRs rather than the entire CDR (see for example, Kashmiri et al., 2005, Methods, 36, 25-34). Humanised antibodies may optionally further comprise one or more framework residues derived from the non-human species from which the CDRs were derived.

Chimeric antibodies are composed of elements derived from two different species such that the elements retain the characteristics of the species from which it is derived. Generally a chimeric antibody will comprise a variable region from one species, for example a mouse, rat, rabbit or similar and constant region from another species such as a human.

The antibodies for use in the present invention can also be generated using various phage display methods known in the art and include those disclosed by Brinkman et al. (in J. Immunol. Methods, 1995, 182: 41-50), Ames et al. (J. Immunol. Methods, 1995, 184:177-186), Kettleborough et al. (Eur. J. Immunol. 1994, 24:952-958), Persic et al. (Gene, 1997 187 9-18), Burton et al. (Advances in Immunology, 1994, 57:191-280) and WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108.

Fully human antibodies are those antibodies in which the variable regions and the constant regions (where present) of both the heavy and the light chains are all of human origin, or substantially identical to sequences of human origin, not necessarily from the same antibody. Examples of fully human antibodies may include antibodies produced, for example by the phage display methods described above and antibodies produced by mice in which the murine immunoglobulin variable and optionally the constant region genes have been replaced by their human counterparts eg. as described in general terms in EP0546073 B1, U.S. Pat. No. 5,545,806, U.S. Pat. No. 5,569,825, U.S. Pat. No. 5,625,126, U.S. Pat. No. 5,633,425, U.S. Pat. No. 5,661,016, U.S. Pat. No. 5,770,429, EP 0438474 and EP0463151.

In one embodiment the present invention provides an antagonistic antibody having specificity for human OX40, comprising a heavy chain, wherein the variable domain of the heavy chain comprises at least one CDR having the sequence given in FIG. 1 (c) SEQ ID NO:1 for CDR-H1, a CDR having the sequence given in FIG. 1(c) SEQ ID NO:2 or SEQ ID NO:20 for CDR-H2 and a CDR having the sequence given in FIG. 1(c) SEQ ID NO:3 for CDR-H3.

In another embodiment the present invention provides an antagonistic antibody having specificity for human OX40, comprising a heavy chain, wherein at least two of CDR-H1, CDR-H2 and CDR-H3 of the variable domain of the heavy chain are selected from the following: the sequence given in SEQ ID NO:1 for CDR-H1, the sequence given in SEQ ID NO:2 for CDR-H2 and the sequence given in SEQ ID NO:3 for CDR-H3. For example, the antibody may comprise a heavy chain wherein CDR-H1 has the sequence given in SEQ ID NO:1 and CDR-H2 has the sequence given in SEQ ID NO:2. Alternatively, the antibody may comprise a heavy chain wherein CDR-H1 has the sequence given in SEQ ID NO:1 and CDR-H3 has the sequence given in SEQ ID NO:3, or the antibody may comprise a heavy chain wherein CDR-H2 has the sequence given in SEQ ID NO:2 and CDR-H3 has the sequence given in SEQ ID NO:3. For the avoidance of doubt, it is understood that all permutations are included.

In another embodiment the present invention provides an antagonistic antibody having specificity for human OX40, comprising a heavy chain, wherein the variable domain of the heavy chain comprises the sequence given in SEQ ID NO:1 for CDR-H1, the sequence given in SEQ ID NO:2 for CDR-H2 and the sequence given in SEQ ID NO:3 for CDR-H3.

In another embodiment the present invention provides an antagonistic antibody having specificity for human OX40, comprising a heavy chain, wherein the variable domain of the heavy chain comprises the sequence given in SEQ ID NO:1 for CDR-H1, the sequence given in SEQ ID NO:20 for CDR-H2 and the sequence given in SEQ ID NO:3 for CDR-H3.

In one embodiment the present invention provides an antagonistic antibody having specificity for human OX40, comprising a light chain, wherein the variable domain of the light chain comprises at least one CDR having the sequence given in FIG. 1 (c) SEQ ID NO:4 or SEQ ID NO:21 for CDR-L1, a CDR having the sequence given in FIG. 1 (c) SEQ ID NO:5 for CDR-L2 and a CDR having the sequence given in FIG. 1 (c) SEQ ID NO:6 for CDR-L3.

In another embodiment the present invention provides an antagonistic antibody having specificity for human OX40, comprising a light chain, wherein at least two of CDR-L1, CDR-L2 and CDR-L3 of the variable domain of the light chain are selected from the following: the sequence given in SEQ ID NO:4 for CDR-L1, the sequence given in SEQ ID NO:5 for CDR-L2 and the sequence given in SEQ ID NO:6 for CDR-L3. For example, the antibody may comprise a light chain wherein CDR-L1 has the sequence given in SEQ ID NO:4 and CDR-L2 has the sequence given in SEQ ID NO:5. Alternatively, the antibody may comprise a light chain wherein CDR-L1 has the sequence given in SEQ ID NO:4 and CDR-L3 has the sequence given in SEQ ID NO:6, or the antibody may comprise a light chain wherein CDR-L2 has the sequence given in SEQ ID NO:5 and CDR-L3 has the sequence given in SEQ ID NO:6. For the avoidance of doubt, it is understood that all permutations are included.

In another embodiment the present invention provides an antagonistic antibody having specificity for human OX40, comprising a light chain, wherein the variable domain comprises the sequence given in SEQ ID NO:4 for CDR-L1, the sequence given in SEQ ID NO:5 for CDR-L2 and the sequence given in SEQ ID NO:6 for CDR-L3.

In another embodiment the present invention provides an antagonistic antibody having specificity for human OX40, comprising a light chain, wherein the variable domain comprises the sequence given in SEQ ID NO:21 for CDR-L1, the sequence given in SEQ ID NO:5 for CDR-L2 and the sequence given in SEQ ID NO:6 for CDR-L3.

The antibody molecules of the present invention suitably comprise a complementary light chain or a complementary heavy chain, respectively.

Hence in one embodiment, an antibody according to the present invention comprises a heavy chain, wherein the variable domain of the heavy chain comprises the sequence given in SEQ ID NO:1 for CDR-H1, the sequence given in SEQ ID NO:2 or SEQ ID NO:20 for CDR-H2 and the sequence given in SEQ ID NO:3 for CDR-H3 and a light chain wherein the variable domain of the light chain comprises the sequence given in SEQ ID NO:4 or SEQ ID NO:21 for CDR-L1, the sequence given in SEQ ID NO:5 for CDR-L2 and the sequence given in SEQ ID NO:6 for CDR-L3.

It will be appreciated that one or more amino acid substitutions, additions and/or deletions may be made to the CDRs provided by the present invention without significantly altering the ability of the antibody to bind to OX40 and to neutralise OX40 activity. The effect of any amino acid substitutions, additions and/or deletions can be readily tested by one skilled in the art, for example by using the methods described herein, in particular in the Examples, to determine OX40 binding and inhibition of the OX40/OX40L interaction. Accordingly, the present invention provides an antibody having specificity for human OX40 comprising one or more CDRs selected from CDRH-1 (SEQ ID NO:1), CDRH-2 (SEQ ID NO:2 or SEQ ID NO:20), CDRH-3 (SEQ ID NO:3), CDRL-1 (SEQ ID NO:4 or SEQ ID NO:21), CDRL-2 (SEQ ID NO:5) and CDRL-3 (SEQ ID NO:6) in which one or more amino acids in one or more of the CDRs has been substituted with another amino acid, suitably a similar amino acid as defined herein below. In one embodiment, the present invention provides an antibody having specificity for human OX40 comprising CDRH-1 (SEQ ID NO:1), CDRH-2 (SEQ ID NO:2 or SEQ ID NO:20), CDRH-3 (SEQ ID NO:3), CDRL-1 (SEQ ID NO:4 or SEQ ID NO:21), CDRL-2 (SEQ ID NO:5) and CDRL-3 (SEQ ID NO:6) as shown in FIG. 1(c), for example in which one or more amino acids in one or more of the CDRs has been substituted with another amino acid, such as a similar amino acid as defined herein below.

In one embodiment, an antibody of the present invention comprises a heavy chain, wherein the variable domain of the heavy chain comprises three CDRs wherein the sequence of CDRH-1 has at least 60% identity or similarity to the sequence given in SEQ ID NO:1, CDRH-2 has at least 60% identity or similarity to the sequence given in SEQ ID NO:2 and/or CDRH-3 has at least 60% identity or similarity to the sequence given in SEQ ID NO:3. In another embodiment, an antibody of the present invention comprises a heavy chain, wherein the variable domain of the heavy chain comprises three CDRs wherein the sequence of CDRH-1 has at least 70%, 80%, 90%, 95% or 98% identity or similarity to the sequence given in SEQ ID NO:1, CDRH-2 has at least 70%, 80%, 90%, 95% or 98% identity or similarity to the sequence given in SEQ ID NO:2 and/or CDRH-3 has at least 70%, 80%, 90%, 95% or 98% identity or similarity to the sequence given in SEQ ID NO:3.

"Identity", as used herein, indicates that at any particular position in the aligned sequences, the amino acid residue is identical between the sequences. "Similarity", as used herein, indicates that, at any particular position in the aligned sequences, the amino acid residue is of a similar type between the sequences. For example, leucine may be substituted for isoleucine or valine. Other amino acids which can often be substituted for one another include but are not limited to:

phenylalanine, tyrosine and tryptophan (amino acids having aromatic side chains);

lysine, arginine and histidine (amino acids having basic side chains);

aspartate and glutamate (amino acids having acidic side chains);

asparagine and glutamine (amino acids having amide side chains); and cysteine and methionine (amino acids having sulphur-containing side chains). Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987, Sequence Analysis Primer, Gribskov, M. and Devereux, J., eds., M Stockton Press, New York, 1991, the BLAST™ software available from NCBI (Altschul, S. F. et al., 1990, J. Mol. Biol. 215:403-410; Gish, W. & States, D. J. 1993, Nature Genet. 3:266-272. Madden, T. L. et al., 1996, Meth. Enzymol. 266:131-141; Altschul, S. F. et al., 1997, Nucleic Acids Res. 25:3389-3402; Zhang, J. & Madden, T. L. 1997, Genome Res. 7:649-656).

In another embodiment, an antibody of the present invention comprises a light chain, wherein the variable domain of the light chain comprises three CDRs wherein the sequence of CDRL-1 has at least 60% identity or similarity to the sequence given in SEQ ID NO:4, CDRL-2 has at least 60% identity or similarity to the sequence given in SEQ ID NO:5 and/or CDRL-3 has at least 60% identity or similarity to the sequence given in SEQ ID NO:6. In another embodiment, an antibody of the present invention comprises a light chain, wherein the variable domain of the light chain comprises three CDRs wherein the sequence of CDRL-1 has at least 70%, 80%, 90%, 95% or 98% identity or similarity to the sequence given in SEQ ID NO:4, CDRL-2 has at least 70%, 80%, 90%, 95% or 98% identity or similarity to the sequence given in SEQ ID NO:5 and/or CDRL-3 has at least 70%, 80%, 90%, 95% or 98% identity or similarity to the sequence given in SEQ ID NO:6.

In one embodiment the antibody provided herein is a monoclonal antibody.

In one embodiment the antibody provided by herein is a chimeric antibody.

In one embodiment the antibody provided by the present invention is a CDR-grafted antibody molecule comprising one or more of the CDRs provided in SEQ ID NOs:1, 2, 3, 4, 5, 6, 20 and/or 21 (FIG. 1 (c)) or variants thereof. As used herein, the term 'CDR-grafted antibody molecule' refers to an antibody molecule wherein the heavy and/or light chain contains one or more CDRs (including, if desired, one or more modified CDRs) from a donor antibody (e.g. a murine monoclonal antibody) grafted into a heavy and/or light chain variable region framework of an acceptor antibody (e.g. a human antibody). For a review, see Vaughan et al, Nature Biotechnology, 16, 535-539, 1998. In one embodiment rather than the entire CDR being transferred, only one or more of the specificity determining residues from any one of the CDRs described herein above are transferred to the human antibody framework (see for example, Kashmiri et al., 2005, Methods, 36, 25-34). In one embodiment only the specificity determining residues from one or more of the CDRs described herein above are transferred to the human antibody framework. In another embodiment only the specificity determining residues from each of the CDRs described herein above are transferred to the human antibody framework.

When the CDRs or specificity determining residues are grafted, any appropriate acceptor variable region framework sequence may be used having regard to the class/type of the donor antibody from which the CDRs are derived, including mouse, primate and human framework regions. Suitably, the CDR-grafted antibody according to the present invention has a variable domain comprising human acceptor framework regions as well as one or more of the CDRs or specificity determining residues described above. Thus, provided in one embodiment is a neutralising CDR-grafted antibody wherein the variable domain comprises human acceptor framework regions and non-human donor CDRs.

Examples of human frameworks which can be used in the present invention are KOL, NEWM, REI, EU, TUR, TEI, LAY and POM (Kabat et al., supra). For example, KOL and NEWM can be used for the heavy chain, REI can be used for the light chain and EU, LAY and POM can be used for both the heavy chain and the light chain. Alternatively, human germline sequences may be used; these are available at: http://vbase.mrc-cpe.cam.ac.uk/

In a CDR-grafted antibody of the present invention, the acceptor heavy and light chains do not necessarily need to be derived from the same antibody and may, if desired, comprise composite chains having framework regions derived from different chains.

The suitable framework region for the heavy chain of the CDR-grafted antibody of the present invention is derived from the human sub-group VH3 sequence 1-3 3-07 together with JH4. Accordingly, provided is a neutralising CDR-grafted antibody comprising at least one non-human donor CDR wherein the heavy chain framework region is derived from the human subgroup VH3 sequence 1-3 3-07 together with JH4. The sequence of human JH4 is as follows: (YFDY) WGQGTLVTVSS (Seq ID No: 22). The YFDY motif is part of CDR-H3 and is not part of framework 4 (Ravetch, J V. et al., 1981, Cell, 27, 583-591).

The suitable framework region for the light chain of the CDR-grafted antibody of the present invention is derived from the human germline sub-group VK1 sequence 2-1 1-02 together with JK4. Accordingly, provided is a neutralising CDR-grafted antibody comprising at least one non-human donor CDR wherein the light chain framework region is derived from the human subgroup sequence 2-1 1-02 together with JK4. The JK1 sequence is as follows: (WT)FGQGT-KVEIK (Seq ID No: 23). The WT motif is part of CDR-L3 and is not part of framework 4 (Hieter, P A, et al., 1982, J. Biol. Chem., 257, 1516-1522).

Also, in a CDR-grafted antibody of the present invention, the framework regions need not have exactly the same sequence as those of the acceptor antibody. For instance, unusual residues may be changed to more frequently-occurring residues for that acceptor chain class or type. Alternatively, selected residues in the acceptor framework regions may be changed so that they correspond to the residue found at the same position in the donor antibody (see Reichmann et al., 1998, Nature, 332, 323-324). Such changes should be kept to the minimum necessary to recover the affinity of the donor antibody. A protocol for selecting residues in the acceptor framework regions which may need to be changed is set forth in WO 91/09967.

Suitably, in a CDR-grafted antibody molecule of the present invention, if the acceptor heavy chain has the human VH3 sequence 1-3 3-07 together with JH4, then the acceptor framework regions of the heavy chain comprise, in addition to one or more donor CDRs, a donor residue at least one of positions 37, 73, 78 or 94 (according to Kabat et al., (supra)). Accordingly, provided is a CDR-grafted antibody, wherein at least the residues at positions 37, 73, 78 and 94 of the variable domain of the heavy chain are donor residues.

Suitably, in a CDR-grafted antibody molecule according to the present invention, if the acceptor light chain has the human sub-group VK1 sequence 2-1 1-02 together with JK4, then the acceptor framework regions of the light chain comprise, in addition to one or more donor CDRs, a donor residue at least one of positions 64 or 71. Accordingly, provided is a CDR-grafted antibody, wherein at least the residues at positions 64 and 71 of the variable domain of the light chain are donor residues.

Donor residues are residues from the donor antibody, i.e. the antibody from which the CDRs were originally derived.

In one embodiment, an antibody of the present invention comprises a heavy chain, wherein the variable domain of the heavy chain comprises the sequence given in FIG. 1 (b) SEQ ID NO:9.

It will be appreciated that one or more amino acid substitutions, additions and/or deletions may be made to the antibody variable domains, provided by the present invention, without significantly altering the ability of the antibody to bind to OX40 and to neutralise OX40 activity. The effect of any amino acid substitutions, additions and/or deletions can be readily tested by one skilled in the art, for example by using the methods described herein, in particular the Examples, to determine OX40 binding and ligand blocking.

In another embodiment, an antibody of the present invention comprises a heavy chain, wherein the variable domain of the heavy chain comprises a sequence having at least 60% identity or similarity to the sequence given in SEQ ID NO:9. In one embodiment, an antibody of the present invention comprises a heavy chain, wherein the variable domain of the heavy chain comprises a sequence having at least 70%, 80%, 90%, 95% or 98% identity or similarity to the sequence given in SEQ ID NO:9.

In one embodiment, an antibody of the present invention comprises a light chain, wherein the variable domain of the light chain comprises the sequence given in FIG. 1 (a) SEQ ID NO:7.

In another embodiment, an antibody of the present invention comprises a light chain, wherein the variable domain of the light chain comprises a sequence having at least 60% identity or similarity to the sequence given in SEQ ID NO:7. In one embodiment the antibody of the present invention comprises a light chain, wherein the variable domain of the light chain comprises a sequence having at least 70%, 80%, 90%, 95% or 98% identity or similarity to the sequence given in SEQ ID NO: 7.

In one embodiment an antibody of the present invention comprises a heavy chain, wherein the variable domain of the heavy chain comprises the sequence given in SEQ ID NO:9 and a light chain, wherein the variable domain of the light chain comprises the sequence given in SEQ ID NO:7.

In another embodiment of the invention, the antibody comprises a heavy chain and a light chain, wherein the variable domain of the heavy chain comprises a sequence having at least 60% identity or similarity to the sequence given in SEQ ID NO:9 and the variable domain of the light chain comprises a sequence having at least 60% identity or similarity to the sequence given in SEQ ID NO:7. Suitably, the antibody comprises a heavy chain, wherein the variable domain of the heavy chain comprises a sequence having at least 70%, 80%, 90%, 95% or 98% identity or similarity to the sequence given in SEQ ID NO:9 and a light chain, wherein the variable domain of the light chain comprises a sequence having at least 70%, 80%, 90%, 95% or 98% identity or similarity to the sequence given in SEQ ID NO:7.

The antibody molecules of the present invention may comprise a complete antibody molecule having full length heavy and light chains or a fragment thereof and may be, but are not limited to Fab, modified Fab, Fab', modified Fab', F(ab').sub.2, Fv, single domain antibodies (e.g. VH or VL or VHH), scFv, bi, tri or tetra-valent antibodies, Bis-scFv, diabodies, triabodies, tetrabodies and epitope-binding fragments of any of the above (see for example Holliger and Hudson, 2005, Nature Biotech. 23(9):1126-1136; Adair and Lawson, 2005, Drug Design Reviews—Online 2(3), 209-217). The methods for creating and manufacturing these antibody fragments are well known in the art (see for example Verma et al., 1998, Journal of Immunological Methods, 216, 165-181). Other antibody fragments for use in the present invention include the Fab and Fab' fragments described in International patent applications WO2005/003169, WO2005/003170 and WO2005/003171. Multi-valent antibodies may comprise multiple specificities or may be monospecific (see for example WO 92/22583 and WO05/113605).

In one embodiment the antibody according to the present disclosure is provided as an OX40 binding antibody fusion protein which comprises an immunoglobulin moiety, for example a Fab or Fab' fragment, and one or two single domain antibodies (dAb) linked directly or indirectly thereto, for example as described in WO2009/040562.

In one embodiment the fusion protein comprises two domain antibodies, for example as a variable heavy (VH) and variable light (VL) pairing, optionally linked by a disulphide bond.

In one embodiment the Fab of Fab' element of the fusion protein has the same or similar specificity to the single domain antibody or antibodies. In one embodiment the Fab or Fab' has a different specificity to the single domain antibody or antibodies, that is to say the fusion protein is multivalent. In one embodiment a multivalent fusion protein according to the present invention has an albumin binding site, for example a VH/VL pair therein provides an albumin binding site.

The constant region domains of the antibody molecule of the present invention, if present, may be selected having regard to the proposed function of the antibody molecule, and in particular the effector functions which may be required. For example, the constant region domains may be human IgA, IgD, IgE, IgG or IgM domains. In particular, human IgG constant region domains may be used, especially of the IgG1 and IgG3 isotypes when the antibody molecule is intended for therapeutic uses and antibody effector functions are required. Alternatively, IgG2 and IgG4 isotypes may be used when the antibody molecule is intended for therapeutic purposes and antibody effector functions are not required, e.g. for simply blocking OX40 activity. It will be appreciated that sequence variants of these constant region domains may also be used. For example IgG4 molecules in which the serine at position 241 has been changed to proline as described in Angal et al., Molecular Immunology, 1993, 30 (1), 105-108 may be used. It will also be understood by one skilled in the art that antibodies may undergo a variety of posttranslational modifications. The type and extent of these modifications often depends on the host cell line used to express the antibody as well as the culture conditions. Such modifications may include variations in glycosylation, methionine oxidation, diketopiperazine formation, aspartate isomerization and asparagine deamidation. A frequent modification is the loss of a carboxy-terminal basic residue (such as lysine or arginine) due to the action of carboxypeptidases (as described in Harris, R J. *Journal of Chromatography* 705:129-134, 1995). Accordingly, the C-terminal lysine of the antibody heavy chain given in FIG. 1 (*f*), SEQ ID NO: 15 may be absent.

In one embodiment the antibody heavy chain comprises a CH1 domain and the antibody light chain comprises a CL domain, either kappa or lambda.

In one embodiment the antibody provided by the present invention is an antagonistic antibody having specificity for human OX40 in which the heavy chain constant region comprises a modified hinge region. Accordingly, the present invention provides an antibody in which the heavy chain comprises or consists of the sequence given in FIG. 1 (*f*), SEQ ID NO:15.

It will be appreciated that one or more amino acid substitutions, additions and/or deletions may be made to the antibody variable and/or constant domains provided by the present invention without significantly altering the ability of the antibody to bind to OX40 and to neutralise OX40 activity. The effect of any amino acid substitutions, additions and/or deletions can be readily tested by one skilled in the art, for example by using the methods described herein, in particular in the Examples, to determine OX40 binding and blocking of the OX40/OX40L interaction.

In one embodiment of the invention, the antibody comprises a heavy chain, wherein the heavy chain comprises a sequence having at least 60% identity or similarity to the sequence given in SEQ ID NO:15. Suitably, the antibody comprises a heavy chain, wherein the heavy chain comprises a sequence having at least 70%, 80%, 90%, 95% or 98% identity or similarity to the sequence given in SEQ ID NO:15.

In one embodiment an antibody molecule according to the present invention comprises a light chain comprising the sequence given in FIG. 1 (*d*), SEQ ID NO:11.

In one embodiment of the invention, the antibody comprises a light chain, wherein the light chain comprises a sequence having at least 60% identity or similarity to the sequence given in SEQ ID NO:11. For example, the antibody comprises a light chain, wherein the light chain comprises a sequence having at least 70%, 80%, 90%, 95% or 98% identity or similarity to the sequence given in SEQ ID NO:11.

In one embodiment the present invention provides an antibody in which the heavy chain comprises or consists of the sequence given in SEQ ID NO:15 and the light chain comprises or consists of the sequence given in SEQ ID NO:11.

In one embodiment of the invention, the antibody comprises a heavy chain and a light chain, wherein the heavy chain comprises a sequence having at least 60% identity or similarity to the sequence given in SEQ ID NO:15 and the light chain comprises a sequence having at least 60% identity or similarity to the sequence given in SEQ ID NO:11. Generally, the antibody comprises a heavy chain, wherein the heavy chain comprises a sequence having at least 70%, 80%, 90%, 95% or 98% identity or similarity to the sequence given in SEQ ID NO:15 and a light chain, wherein the light chain comprises a sequence having at least 70%, 80%, 90%, 95% or 98% identity or similarity to the sequence given in SEQ ID NO:11.

Biological molecules, such as antibodies or fragments, contain acidic and/or basic functional groups, thereby giving the molecule a net positive or negative charge. The amount of overall "observed" charge will depend on the absolute amino acid sequence of the entity, the local environment of the charged groups in the 3D structure and the environmental conditions of the molecule. The isoelectric point (pI) is the pH at which a particular molecule or solvent accessible surface thereof carries no net electrical charge. In one embodiment the antibody or fragment according to the present disclosure has an isoelectric point (pI) of at least 7. In one embodiment the antibody or fragment has an isoelectric point of at least 8, such as 8.5, 8.6, 8.7, 8.8 or 9.

The OX40 antibody and fragments of the invention have been engineered to have an appropriate isoelectric point. This may lead to antibodies and/or fragments with more robust properties, in particular suitable solubility and/or stability profiles and/or improved purification characteristics.

Thus in one aspect the invention provides a humanised OX40 antibody engineered to have an isoelectric point different to that of the originally identified antibody CA044__00026. The antibody may, for example be engineered by replacing an amino acid residue such as replacing an acidic amino acid residue with one or more basic amino acid residues. Alternatively, basic amino acid residues may be introduced or acidic amino acid residues can be removed. Alternatively, if the molecule has an unacceptably high pI value acidic residues may be introduced to lower the pI, as required. The target pI of the engineered antibody or fragment desirably may, for example be 8 or above, such 8.5 or 9. It is important that when manipulating the pI care must be taken to retain the desirable activity of the antibody or fragment. Thus in one embodiment the engineered antibody or fragment has the same or substantially the same activity as the "unmodified" antibody or fragment.

Programs such as ** ExPASY http://www.expasy.ch/tools/pi_tool.html, and http://www.iut-arles.up.univ-mrs.fr/w3bb/d_abim/compo-p.html, may be used to predict the isoelectric point of the antibody or fragment.

Also provided by the present invention is a specific region or epitope of human OX40 which is bound by an antibody provided by the present invention, in particular an antibody comprising the heavy chain sequence gH2 (SEQ ID NO:9) and/or the light chain sequence gL8 (SEQ ID NO:7).

This specific region or epitope of the human OX40 polypeptide can be identified by any suitable epitope mapping method known in the art in combination with any one of the antibodies provided by the present invention. Examples of such methods include screening peptides of varying lengths derived from OX40 for binding to the antibody of the present invention with the smallest fragment that can specifically bind to the antibody containing the sequence of the epitope recognised by the antibody. The OX40 peptides may be produced synthetically or by proteolytic digestion of the OX40 polypeptide. Peptides that bind the antibody can be identified by, for example, mass spectrometric analysis. In another example, NMR spectroscopy or X-ray crystallography can be used to identify the epitope bound by an antibody of the present invention. Once identified, the epitopic fragment which binds an antibody of the present invention can be used, if required, as an immunogen to obtain additional antagonistic antibodies which bind the same epitope.

Antibodies which cross-block the binding of an antibody according to the present invention in particular, an antibody comprising the heavy chain sequence gH2 (SEQ ID NO:9) and the light chain sequence gL8 (SEQ ID NO:7) may be similarly useful in antagonising OX40 activity. Accordingly, the present invention also provides an antagonistic antibody having specificity for human OX40, which cross-blocks the binding of any one of the antibodies described above to human OX40 and/or is cross-blocked from binding OX40 by any one of those antibodies. In one embodiment, such an antibody binds to the same epitope as an antibody described herein above. In another embodiment the cross-blocking neutralising antibody binds to an epitope which borders and/or overlaps with the epitope bound by an antibody described herein above. In another embodiment the cross-blocking neutralising antibody of this aspect of the invention does not bind to the same epitope as an antibody of the present invention or an epitope that borders and/or overlaps with said epitope.

Cross-blocking antibodies can be identified using any suitable method in the art, for example by using competition ELISA or BIAcore assays where binding of the cross blocking antibody to human OX40 prevents the binding of an antibody of the present invention or vice versa.

In one embodiment there is provided an antagonistic antibody having specificity for human OX40, which cross-blocks the binding of an antibody whose heavy chain comprises the sequence gH2 (SEQ ID NO:9) and whose light chain comprises the sequence gL8 (SEQ ID NO:7) to human OX40. In one embodiment the cross-blocking antibodies provided by the present invention inhibit the binding of an antibody comprising the heavy chain sequence gH2 (SEQ ID NO:9) and the light chain sequence gL8 (SEQ ID NO:7) by greater than 80%, for example by greater than 85%, such as by greater than 90%, in particular by greater than 95%.

Alternatively or in addition, antagonistic antibodies according to this aspect of the invention may be cross-blocked from binding to human OX40 by an antibody comprising the heavy chain sequence gH2 (SEQ ID NO:9) and the light chain sequence gL8 (SEQ ID NO:7). Also provided therefore is an antagonistic antibody molecule having specificity for human OX40 which is cross-blocked from binding human OX40 by an antibody comprising the heavy chain sequence gH2 (SEQ ID NO:9) and the light chain sequence gL8 (SEQ ID NO:7). In one embodiment the antagonistic antibodies provided by this aspect of the invention are inhibited from binding human OX40 by an antibody comprising the heavy chain sequence gH2 (SEQ ID NO:9) and the light chain sequence gL8 (SEQ ID NO:7) by greater than 80%, for example by greater than 85%, such as by greater than 90%, in particular by greater than 95%.

In one embodiment the cross-blocking antibodies provided by the present invention are fully human. In one embodiment the cross-blocking antibodies provided by the present invention are humanised. In one embodiment the cross-blocking antibodies provided by the present invention have an affinity for human OX40 of 100 pM or better. In one embodiment the cross-blocking antibodies provided by the present invention have an affinity for human OX40 of 50 pM or better.

In one embodiment the cross-blocking antibody has an isoelectric point of at least 7, for example at least 8, such as 8.5, 8.6, 8.7, 8.8, 8.9 or 9.0.

The antibody molecules of the present invention suitably have a high binding affinity, in particular picomolar. Affinity may be measured using any suitable method known in the art, including BIAcore, as described in the Examples herein, using isolated natural or recombinant OX40 or a suitable fusion protein/polypeptide. In one example affinity is measured using recombinant human OX40 extracellular domain as described in the Examples herein. In one example the recombinant human OX40 extracellular domain used is a dimer, for example an Fc fusion dimer. Suitably the antibody molecules of the present invention have a binding affinity for isolated human OX40 of about 200 pM or better. In one embodiment the antibody molecule of the present invention has a binding affinity of about 100 pM or better. In one embodiment the antibody molecule of the present invention has a binding affinity of about 50 pM or better. In one embodiment the antibody molecule of the present invention has a binding affinity of about 40 pM or better. In one embodiment the antibody molecule of the present invention has a binding affinity of about 30 pM or better. In one embodiment the antibody molecule of the present invention is fully human or humanised and has a binding affinity of about 100 pM or better.

The antibody molecules of the present invention suitably have a high binding affinity for human OX40 expressed on the surface of activated T cells, for example nanomolar or picomolar affinity. Affinity may be measured using any suitable method known in the art, including the method as described in the Examples herein using activated CD4$^+$ OX40$^+$ human T cells. In particular the antibody molecules of the present invention have a binding affinity for cell surface expressed human OX40 of about 2 nM or better. In one example the antibody molecules of the present invention have a binding affinity for cell surface expressed human OX40 of about 1.5 nM or better. In another example the antibody molecules of the present invention have a binding affinity for cell surface expressed human OX40 of about 1.2 nM or better. In one embodiment there is provided a fully human or humanised antibody molecule which has a binding affinity of about 2 nM or better for human cell surface expressed OX40.

It will be appreciated that the affinity of antibodies provided by the present invention may be altered using any suitable method known in the art. The present invention therefore also relates to variants of the antibody molecules of the present invention, which have an improved affinity for OX40. Such variants can be obtained by a number of affinity maturation protocols including mutating the CDRs (Yang et al., J. Mol. Biol., 254, 392-403, 1995), chain shuffling (Marks et al., Bio/Technology, 10, 779-783, 1992), use of mutator strains of E. coli (Low et al., J. Mol. Biol., 250, 359-368, 1996), DNA shuffling (Patten et al., Curr. Opin. Biotechnol., 8, 724-733, 1997), phage display (Thompson et al., J. Mol. Biol., 256, 77-88, 1996) and sexual PCR (Crameri et al., Nature, 391, 288-291, 1998). Vaughan et al. (supra) discusses these methods of affinity maturation.

In one embodiment the antibody molecules of the present invention block the interaction between OX40 and OX40L. Numerous assays suitable for determining the ability of an antibody to block this interaction are described in the examples herein. In one embodiment the present invention provides a neutralising antibody having specificity for human OX40 which is capable of inhibiting the binding of human OX40L (tested at a final concentration of 2 μg/ml) to activated human CD4+OX40+ T cells by 50% at a concentration of less than 5 nM. In one embodiment the human OX40L used in the assay is natural human OX40. In one embodiment the human OX40 used in the assay is recombinant human OX40. In one embodiment the neutralising antibody is a humanised or fully human antibody.

If desired an antibody for use in the present invention may be conjugated to one or more effector molecule(s). It will be appreciated that the effector molecule may comprise a single effector molecule or two or more such molecules so linked as to form a single moiety that can be attached to the antibodies of the present invention. Where it is desired to obtain an antibody fragment linked to an effector molecule, this may be prepared by standard chemical or recombinant DNA procedures in which the antibody fragment is linked either directly or via a coupling agent to the effector molecule. Techniques for conjugating such effector molecules to antibodies are well known in the art (see, Hellstrom et al., Controlled Drug Delivery, 2nd Ed., Robinson et al., eds., 1987, pp. 623-53; Thorpe et al., 1982, Immunol. Rev., 62:119-58 and Dubowchik et al., 1999, Pharmacology and Therapeutics, 83, 67-123). Particular chemical procedures include, for example, those described in WO 93/06231, WO 92/22583, WO 89/00195, WO 89/01476 and WO03031581. Alternatively, where the effector molecule is a protein or polypeptide the linkage may be achieved using recombinant DNA procedures, for example as described in WO 86/01533 and EP0392745.

The term effector molecule as used herein includes, for example, antineoplastic agents, drugs, toxins, biologically active proteins, for example enzymes, other antibody or antibody fragments, synthetic or naturally occurring polymers, nucleic acids and fragments thereof e.g. DNA, RNA and fragments thereof, radionuclides, particularly radioiodide, radioisotopes, chelated metals, nanoparticles and reporter groups such as fluorescent compounds or compounds which may be detected by NMR or ESR spectroscopy.

Examples of effector molecules may include cytotoxins or cytotoxic agents including any agent that is detrimental to (e.g. kills) cells. Examples include combrestatins, dolastatins, epothilones, staurosporin, maytansinoids, spongistatins, rhizoxin, halichondrins, roridins, hemiasterlins, taxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

Effector molecules also include, but are not limited to, antimetabolites (e.g. methotrexate, 6-mercaptopurine, 6-thioguanine, cytarabine, 5-fluorouracil decarbazine), alkylating agents (e.g. mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum (II) (DDP) cisplatin), anthracyclines (e.g. daunorubicin (formerly daunomycin) and doxorubicin), antibiotics (e.g. dactinomycin (formerly actinomycin), bleomycin, mithramycin, anthramycin (AMC), calicheamicins or duocarmycins), and anti-mitotic agents (e.g. vincristine and vinblastine).

Other effector molecules may include chelated radionuclides such as $^{111}$In and $^{90}$Y, $Lu^{177}$, $Bismuth^{213}$, $Californium^{252}$, $Iridium^{192}$ and $Tungsten^{188}/Rhenium^{188}$; or drugs such as but not limited to, alkylphosphocholines, topoisomerase I inhibitors, taxoids and suramin.

Other effector molecules include proteins, peptides and enzymes. Enzymes of interest include, but are not limited to, proteolytic enzymes, hydrolases, lyases, isomerases, transferases.

Proteins, polypeptides and peptides of interest include, but are not limited to, immunoglobulins, toxins such as abrin, ricin A, pseudomonas exotoxin, or diphtheria toxin, a protein such as insulin, tumour necrosis factor, α-interferon, β-interferon, nerve growth factor, platelet derived growth factor or tissue plasminogen activator, a thrombotic agent or an antiangiogenic agent, e.g. angiostatin or endostatin, or, a biological response modifier such as a lymphokine, interleukin-1 (IL-1), interleukin-2 (IL-2), granulocyte macrophage colony stimulating factor (GM-CSF), granulocyte colony stimulating factor (G-CSF), nerve growth factor (NGF) or other growth factor and immunoglobulins.

Other effector molecules may include detectable substances useful for example in diagnosis. Examples of detectable substances include various enzymes, prosthetic groups, fluorescent materials, luminescent materials, bioluminescent materials, radioactive nuclides, positron emitting metals (for use in positron emission tomography), and nonradioactive paramagnetic metal ions. See generally U.S. Pat. No. 4,741,900 for metal ions which can be conjugated to antibodies for use as diagnostics. Suitable enzymes include horseradish peroxidase, alkaline phosphatase, beta-galactosidase, or acetylcholinesterase; suitable prosthetic groups include streptavidin, avidin and biotin; suitable fluorescent materials include umbelliferone, fluorescein, fluorescein isothiocyanate, rhodamine, dichlorotriazinylamine fluorescein, dansyl chloride and phycoerythrin; suitable luminescent materials include luminol; suitable bioluminescent materials include luciferase, luciferin, and aequorin; and suitable radioactive nuclides include $^{125}$I, $^{131}$I, $^{111}$In and $^{99}$Tc.

In another example the effector molecule may increase the half-life of the antibody in vivo, and/or reduce immunogenicity of the antibody and/or enhance the delivery of an antibody across an epithelial barrier to the immune system. Examples of suitable effector molecules of this type include polymers, albumin, albumin binding proteins or albumin binding compounds such as those described in WO05/117984.

Where the effector molecule is a polymer it may, in general, be a synthetic or a naturally occurring polymer, for example an optionally substituted straight or branched chain polyalkylene, polyalkenylene or polyoxyalkylene polymer or a branched or unbranched polysaccharide, e.g. a homo- or hetero-polysaccharide.

Specific optional substituents which may be present on the above-mentioned synthetic polymers include one or more hydroxy, methyl or methoxy groups.

Specific examples of synthetic polymers include optionally substituted straight or branched chain poly(ethyleneglycol), poly(propyleneglycol) poly(vinylalcohol) or derivatives thereof, especially optionally substituted poly(ethyleneglycol) such as methoxypoly(ethyleneglycol) or derivatives thereof.

Specific naturally occurring polymers include lactose, amylose, dextran, glycogen or derivatives thereof.

"Derivatives" as used herein is intended to include reactive derivatives, for example thiol-selective reactive groups such as maleimides and the like. The reactive group may be linked directly or through a linker segment to the polymer. It will be appreciated that the residue of such a group will in some instances form part of the product as the linking group between the antibody fragment and the polymer.

The size of the polymer may be varied as desired, but will generally be in an average molecular weight range from 500 Da to 50000 Da, for example from 5000 to 40000 Da such as from 20000 to 40000 Da. The polymer size may in particular be selected on the basis of the intended use of the product for example ability to localize to certain tissues such as tumors or extend circulating half-life (for review see Chapman, 2002, Advanced Drug Delivery Reviews, 54, 531-545). Thus, for example, where the product is intended to leave the circulation and penetrate tissue, for example for use in the treatment of a tumour, it may be advantageous to use a small molecular weight polymer, for example with a molecular weight of around 5000 Da. For applications where the product remains in the circulation, it may be advantageous to use a higher molecular weight polymer, for example having a molecular weight in the range from 20000 Da to 40000 Da.

Suitable polymers include a polyalkylene polymer, such as a poly(ethyleneglycol) or, especially, a methoxypoly(ethyleneglycol) or a derivative thereof, and especially with a molecular weight in the range from about 15000 Da to about 40000 Da.

In one example antibodies for use in the present invention are attached to poly(ethyleneglycol) (PEG) moieties. In one particular example the antibody is an antibody fragment and the PEG molecules may be attached through any available amino acid side-chain or terminal amino acid functional group located in the antibody fragment, for example any free amino, imino, thiol, hydroxyl or carboxyl group. Such amino acids may occur naturally in the antibody fragment or may be engineered into the fragment using recombinant DNA methods (see for example U.S. Pat. No. 5,219,996; U.S. Pat. No. 5,677,425; WO98/25971). In one example the antibody molecule of the present invention is a modified Fab fragment wherein the modification is the addition to the C-terminal end of its heavy chain one or more amino acids to allow the attachment of an effector molecule. Suitably, the additional amino acids form a modified hinge region containing one or more cysteine residues to which the effector molecule may be attached. Multiple sites can be used to attach two or more PEG molecules.

Suitably PEG molecules are covalently linked through a thiol group of at least one cysteine residue located in the antibody fragment. Each polymer molecule attached to the modified antibody fragment may be covalently linked to the sulphur atom of a cysteine residue located in the fragment. The covalent linkage will generally be a disulphide bond or, in particular, a sulphur-carbon bond. Where a thiol group is used as the point of attachment appropriately activated effector molecules, for example thiol selective derivatives such as maleimides and cysteine derivatives may be used. An activated polymer may be used as the starting material in the preparation of polymer-modified antibody fragments as described above. The activated polymer may be any polymer containing a thiol reactive group such as an α-halocarboxylic acid or ester, e.g. iodoacetamide, an imide, e.g. maleimide, a vinyl sulphone or a disulphide. Such starting materials may be obtained commercially (for example from Nektar, formerly Shearwater Polymers Inc., Huntsville, Ala., USA) or may be prepared from commercially available starting materials using conventional chemical procedures. Particular PEG molecules include 20K methoxy-PEG-amine (obtainable from Nektar, formerly Shearwater; Rapp Polymere; and Sun-Bio) and M-PEG-SPA (obtainable from Nektar, formerly Shearwater).

In one embodiment, the antibody is a modified Fab fragment or diFab which is PEGylated, i.e. has PEG (poly(ethyleneglycol)) covalently attached thereto, e.g. according to the method disclosed in EP 0948544 or EP1090037 [see also "Poly(ethyleneglycol) Chemistry, Biotechnical and Biomedical Applications", 1992, J. Milton Harris (ed), Plenum Press, New York, "Poly(ethyleneglycol) Chemistry and Biological Applications", 1997, J. Milton Harris and S. Zalipsky (eds), American Chemical Society, Washington D.C. and "Bioconjugation Protein Coupling Techniques for the Biomedical Sciences", 1998, M. Aslam and A. Dent, Grove Publishers, New York; Chapman, A. 2002, Advanced Drug Delivery Reviews 2002, 54:531-545]. In one example PEG is attached to a cysteine in the hinge region. In one example, a PEG modified Fab fragment has a maleimide group covalently linked to a single thiol group in a modified hinge region. A lysine residue may be covalently linked to the maleimide group and to each of the amine groups on the lysine residue may be attached a methoxypoly(ethyleneglycol) polymer having a molecular weight of approximately 20,000 Da. The total molecular weight of the PEG attached to the Fab fragment may therefore be approximately 40,000 Da.

In one embodiment, the present invention provides an antagonistic antibody molecule having specificity for human OX40, which is a modified Fab fragment having a heavy chain comprising the sequence given in SEQ ID NO:9 and a light chain comprising the sequence given in SEQ ID NO:7 and having at the C-terminal end of its heavy chain a modified hinge region containing at least one cysteine residue to which an effector molecule is attached. Suitably the effector molecule is PEG and is attached using the methods described in (WO98/25971 and WO2004072116 or in WO2007/003898). Suitably the effector molecule is attached in such as way that a lysyl-maleimide group is attached to the cysteine residue at the C-terminal end of the heavy chain, and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da. Particular PEG molecules include 2-[3-(N-maleimido)propionamido] ethyl amide of N,N'-bis(methoxypoly(ethylene glycol) MW 20,000) modified lysine, also known as PEG2MAL40K (obtainable from Nektar, formerly Shearwater).

Alternative sources of PEG linkers include NOF who supply GL2-400MA2 (wherein m in the structure below is 5) and GL2-400MA (where m is 2) and n is approximately 450:

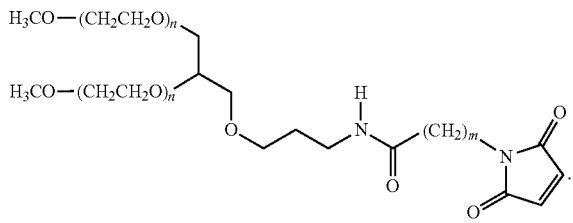

m is 2 or 5

That is to say each PEG is about 20,000 Da.
Further alternative PEG effector molecules of the following type:

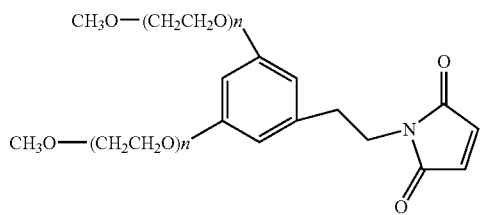

are available from Dr Reddy, NOF and Jenkem.

In one embodiment there is provided an antibody which is PEGylated (for example with a PEG described herein), attached through a cysteine amino acid residue at or about amino acid 226 in the chain, for example amino acid 226 of the heavy chain (by sequential numbering).

In one embodiment, the present invention provides an antagonistic antibody molecule having specificity for human OX40, which is a modified Fab fragment having a heavy chain comprising or consisting of the sequence given in SEQ ID NO:15 and a light chain comprising or consisting of the sequence given in SEQ ID NO:11 and having an effector molecule attached to the cysteine at position 226 of the heavy chain (linear numbering from SEQ ID NO:15). Suitably the effector molecule is PEG and is attached using the methods described in (WO98/25971 and WO2004072116 or WO2007/003898) and a lysyl-maleimide group is attached to the cysteine residue at position 226 of the heavy chain (SEQ ID NO:15), and each amino group of the lysyl residue has covalently linked to it a methoxypoly(ethyleneglycol) residue having a molecular weight of about 20,000 Da. The total molecular weight of the PEG attached to the antibody is therefore approximately 40,000 Da. Particular PEG molecules include 2-[3-(N-maleimido)propionamido]ethyl amide of N,N'-bis(methoxypoly(ethylene glycol) MW 20,000) modified lysine, also known as PEG2MAL40K (obtainable from Nektar, formerly Shearwater). Suitably, the antibody molecule of the present invention is a PEGylated modified Fab' fragment as shown in FIG. 2. This PEGylated molecule is referred to herein as A26Fab'-PEG.

In another example effector molecules may be attached to antibody fragments using the methods described in applications WO2005/003169, WO2005/003170 & WO2005/003171.

The present invention also provides an isolated DNA sequence encoding the heavy and/or light chain(s) of an antibody molecule of the present invention. Suitably, the DNA sequence encodes the heavy or the light chain of an antibody molecule of the present invention. The DNA sequence of the present invention may comprise synthetic DNA, for instance produced by chemical processing, cDNA, genomic DNA or any combination thereof. DNA sequences which encode an antibody molecule of the present invention can be obtained by methods well known to those skilled in the art. For example, DNA sequences coding for part or all of the antibody heavy and light chains may be synthesised as desired from the determined DNA sequences or on the basis of the corresponding amino acid sequences.

DNA coding for acceptor framework sequences is widely available to those skilled in the art and can be readily synthesised on the basis of their known amino acid sequences.

Standard techniques of molecular biology may be used to prepare DNA sequences coding for the antibody molecule of the present invention. Desired DNA sequences may be synthesised completely or in part using oligonucleotide synthesis techniques. Site-directed mutagenesis and polymerase chain reaction (PCR) techniques may be used as appropriate.

Examples of suitable sequences are provided in FIG. 1 (h) SEQ ID NO:8; FIG. 1 (i) SEQ ID NO:10; FIG. 1 (j) SEQ ID NO:13; FIG. 1 (k) SEQ ID NO:14; FIG. 1 (l) SEQ ID NO:17 and FIG. 1 (m) SEQ ID NO:18. Nucleotides 1-63 in SEQ ID NO 18 and 1-63 in SEQ ID NO:14 encode the signal peptide sequence OmpA which is cleaved to give an antagonistic antibody molecule of the present invention (the signal peptide corresponds to amino acid residues 1-21 in FIG. 1 (g) SEQ ID NO: 16 and 1-21 in FIG. 1 (e) SEQ ID NO:12 respectively). The present invention also provides an isolated DNA sequence encoding the heavy chain of an antibody of the present invention which comprises SEQ ID NO:17 or SEQ ID NO:18. The present invention also provides an isolated DNA sequence encoding the light chain of an antibody of the present invention which comprises SEQ ID NO:13 or SEQ ID NO:14.

The present invention also relates to a cloning or expression vector comprising one or more DNA sequences of the present invention. Accordingly, provided is a cloning or expression vector comprising one or more DNA sequences encoding an antibody of the present invention. Suitably, the cloning or expression vector comprises two DNA sequences, encoding the light chain and the heavy chain of the antibody molecule of the present invention, respectively. Suitably, a vector according to the present invention comprises the sequences given in SEQ ID NO:14 and SEQ ID NO:18. Nucleotides 1-63 in SEQ ID NO 18 and 1-63 in SEQ ID NO 14 encode the signal peptide sequence from OmpA (residues 1-21 in SEQ ID NO: 16 and 1-21 in SEQ ID NO:12 respectively) which is most suitably cleaved to give a neutralising antibody molecule of the present invention. In one example the vector comprises an intergenic sequence between the heavy and the light chains, such as IGS2 (see WO03/048208). Accordingly in one embodiment the vector of the present invention comprises the sequence given in FIG. 1 (n) (SEQ ID NO:19).

General methods by which the vectors may be constructed, transfection methods and culture methods are well known to those skilled in the art. In this respect, reference is made to "Current Protocols in Molecular Biology", 1999, F. M. Ausubel (ed), Wiley Interscience, New York and the Maniatis Manual produced by Cold Spring Harbor Publishing.

Also provided is a host cell comprising one or more cloning or expression vectors comprising one or more DNA sequences encoding an antibody of the present invention. Any suitable host cell/vector system may be used for expression of the DNA sequences encoding the antibody molecule of the present invention. Bacterial, for example *E. coli*, and other microbial systems may be used or eukaryotic, for example mammalian, host cell expression systems may also be used. Suitable mammalian host cells include CHO, myeloma or hybridoma cells.

The present invention also provides a process for the production of an antibody molecule according to the present invention comprising culturing a host cell containing a vector of the present invention under conditions suitable for leading to expression of protein from DNA encoding the antibody molecule of the present invention, and isolating the antibody molecule.

The antibody molecule may comprise only a heavy or light chain polypeptide, in which case only a heavy chain or light chain polypeptide coding sequence needs to be used to transfect the host cells. For production of products comprising both heavy and light chains, the cell line may be transfected with two vectors, a first vector encoding a light chain polypeptide and a second vector encoding a heavy chain polypeptide. Alternatively, a single vector may be used, the vector including sequences encoding light chain and heavy chain polypeptides.

The antibodies and fragments according to the present disclosure are expressed at good levels from host cells. Thus the properties of the antibodies and/or fragments are optimised and condusive to commercial processing.

As the antibodies of the present invention are useful in the treatment and/or prophylaxis of a pathological condition, the present invention also provides a pharmaceutical or diagnostic composition comprising an antibody molecule of the present invention in combination with one or more of a pharmaceutically acceptable excipient, diluent or carrier. Accordingly, provided is the use of an antibody of the invention for the manufacture of a medicament. The composition will usually be supplied as part of a sterile, pharmaceutical composition that will normally include a pharmaceutically acceptable carrier. A pharmaceutical composition of the present invention may additionally comprise a pharmaceutically-acceptable adjuvant.

The present invention also provides a process for preparation of a pharmaceutical or diagnostic composition comprising adding and mixing the antibody molecule of the present invention together with one or more of a pharmaceutically acceptable excipient, diluent or carrier.

The antibody molecule may be the sole active ingredient in the pharmaceutical or diagnostic composition or may be accompanied by other active ingredients including other antibody ingredients, for example anti-TNF, anti-IL-1β, anti-T cell, anti-IFNγ or anti-LPS antibodies, or non-antibody ingredients such as xanthines. Other suitable active ingredients include antibodies capable of inducing tolerance, for example, anti-CD3 or anti-CD4 antibodies.

In a further embodiment the antibody, fragment or composition according to the disclosure is employed in combination with a further pharmaceutically active agent, for example a corticosteroid (such as fluticasonoe propionate) and/or a beta-2-agonist (such as salbutamol, salmeterol or formoterol) or inhibitors of cell growth and proliferation (such as rapamycin, cyclophosphmide, methotrexate) or alternative a CD28 and/or CD40 inhibitor. In one embodiment the inhibitor is a small molecule. In another embodiment the inhibitor is an antibody specific to the target.

The pharmaceutical compositions suitably comprise a therapeutically effective amount of the antibody of the invention. The term "therapeutically effective amount" as used herein refers to an amount of a therapeutic agent needed to treat, ameliorate or prevent a targeted disease or condition, or to exhibit a detectable therapeutic or preventative effect. For any antibody, the therapeutically effective amount can be estimated initially either in cell culture assays or in animal models, usually in rodents, rabbits, dogs, pigs or primates. The animal model may also be used to determine the appropriate concentration range and route of administration. Such information can then be used to determine useful doses and routes for administration in humans.

The precise therapeutically effective amount for a human subject will depend upon the severity of the disease state, the general health of the subject, the age, weight and gender of the subject, diet, time and frequency of administration, drug combination(s), reaction sensitivities and tolerance/response to therapy. This amount can be determined by routine experimentation and is within the judgement of the clinician. Generally, a therapeutically effective amount will be from 0.01 mg/kg to 50 mg/kg, for example 0.1 mg/kg to 20 mg/kg. Pharmaceutical compositions may be conveniently presented in unit dose forms containing a predetermined amount of an active agent of the invention per dose.

Compositions may be administered individually to a patient or may be administered in combination (e.g. simultaneously, sequentially or separately) with other agents, drugs or hormones.

The dose at which the antibody molecule of the present invention is administered depends on the nature of the condition to be treated, the extent of the inflammation present and on whether the antibody molecule is being used prophylactically or to treat an existing condition.

The frequency of dose will depend on the half-life of the antibody molecule and the duration of its effect. If the antibody molecule has a short half-life (e.g. 2 to 10 hours) it may be necessary to give one or more doses per day. Alternatively, if the antibody molecule has a long half life (e.g. 2 to 15 days) it may only be necessary to give a dosage once per day, once per week or even once every 1 or 2 months.

The pharmaceutically acceptable carrier should not itself induce the production of antibodies harmful to the individual receiving the composition and should not be toxic. Suitable carriers may be large, slowly metabolised macromolecules such as proteins, polypeptides, liposomes, polysaccharides, polylactic acids, polyglycolic acids, polymeric amino acids, amino acid copolymers and inactive virus particles.

Pharmaceutically acceptable salts can be used, for example mineral acid salts, such as hydrochlorides, hydrobromides, phosphates and sulphates, or salts of organic acids, such as acetates, propionates, malonates and benzoates.

Pharmaceutically acceptable carriers in therapeutic compositions may additionally contain liquids such as water, saline, glycerol and ethanol. Additionally, auxiliary substances, such as wetting or emulsifying agents or pH buffering substances, may be present in such compositions. Such carriers enable the pharmaceutical compositions to be formulated as tablets, pills, dragees, capsules, liquids, gels, syrups, slurries and suspensions, for ingestion by the patient.

Suitable forms for administration include forms suitable for parenteral administration, e.g. by injection or infusion, for example by bolus injection or continuous infusion. Where the product is for injection or infusion, it may take the form of a suspension, solution or emulsion in an oily or aqueous vehicle and it may contain formulatory agents, such as suspending, preservative, stabilising and/or dispersing agents. Alternatively, the antibody molecule may be in dry form, for reconstitution before use with an appropriate sterile liquid.

Once formulated, the compositions of the invention can be administered directly to the subject. The subjects to be treated can be animals. However, in one or more embodiments the compositions are adapted for administration to human subjects.

Suitably in formulations according to the present disclosure, the pH of the final formulation is not similar to the value of the isoelectric point of the antibody or fragment, for example if the pH of the formulation is 7 then a pI of from 8-9 or above may be appropriate. Whilst not wishing to be bound by theory it is thought that this may ultimately provide a final formulation with improved stability, for example the antibody or fragment remains in solution.

In one embodiment the pharmaceutical formulation at a pH in the range of 4.0 to 7.0 comprises: 1 to 200 mg/mL of an antibody according to the present disclosure, 1 to 100 mM of a buffer, 0.001 to 1% of a surfactant, a) 10 to 500 mM of a stabiliser, b) 10 to 500 mM of a stabiliser and 5 to 500 mM of a tonicity agent, or c) 5 to 500 mM of a tonicity agent.

For example the formulation at approximately pH6 may comprise 1 to 50 mg/mL of antibody, 20 mM L-histidine HCl, 240 mM trehalose and 0.02% polysorbate 20. Alternatively a formulation at approximately pH 5.5 may comprise 1 to 50 mg/mL of antibody, 20 mM citrate buffer, 240 mM sucrose, 20 mM arginine, and 0.02% polysorbate 20.

The pharmaceutical compositions of this invention may be administered by any number of routes including, but not limited to, oral, intravenous, intramuscular, intra-arterial, intramedullary, intrathecal, intraventricular, transdermal, transcutaneous (for example, see WO98/20734), subcutaneous, intraperitoneal, intranasal, enteral, topical, sublingual, intravaginal or rectal routes. Hyposprays may also be used to administer the pharmaceutical compositions of the invention. Typically, the therapeutic compositions may be prepared as injectables, either as liquid solutions or suspensions. Solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. The compositions can also be administered into a lesion. Dosage treatment may be a single dose schedule or a multiple dose schedule.

It will be appreciated that the active ingredient in the composition will be an antibody molecule. As such, it will be susceptible to degradation in the gastrointestinal tract. Thus, if the composition is to be administered by a route using the gastrointestinal tract, the composition will need to contain agents which protect the antibody from degradation but which release the antibody once it has been absorbed from the gastrointestinal tract.

A thorough discussion of pharmaceutically acceptable carriers is available in Remington's Pharmaceutical Sciences (Mack Publishing Company, N.J. 1991).

In one embodiment the formulation is provided as a formulation for topical administrations including inhalation.

Suitable inhalable preparations include inhalable powders, metering aerosols containing propellant gases or inhalable solutions free from propellant gases. Inhalable powders according to the disclosure containing the active substance may consist solely of the above-mentioned active substances or of a mixture of the abovementioned active substances with physiologically acceptable excipient.

These inhalable powders may include monosaccharides (e.g. glucose or arabinose), disaccharides (e.g. lactose, saccharose, maltose), oligo- and polysaccharides (e.g. dextranes), polyalcohols (e.g. sorbitol, mannitol, xylitol), salts (e.g. sodium chloride, calcium carbonate) or mixtures of these with one another. Mono- or disaccharides are suitably used, the use of lactose or glucose, particularly but not exclusively in the form of their hydrates.

Particles for deposition in the lung require a particle size less than 10 microns, such as 1-9 microns for example from 0.1 to 5 μm, in particular from 1 to 5 μm. The particle size of the active ingredient (such as the antibody or fragment) is of primary importance.

The propellent gases which can be used to prepare the inhalable aerosols are known in the art. Suitable propellent gases are selected from among hydrocarbons such as n-propane, n-butane or isobutane and halohydrocarbons such as chlorinated and/or fluorinated derivatives of methane, ethane, propane, butane, cyclopropane or cyclobutane. The abovementioned propellent gases may be used on their own or in mixtures thereof.

Particularly suitable propellent gases are halogenated alkane derivatives selected from among TG 11, TG 12, TG 134a and TG227. Of the abovementioned halogenated hydrocarbons, TG134a (1,1,1,2-tetrafluoroethane) and TG227 (1,1,1,2,3,3,3-heptafluoropropane) and mixtures thereof are particularly suitable.

The propellent-gas-containing inhalable aerosols may also contain other ingredients such as cosolvents, stabilisers, surface-active agents (surfactants), antioxidants, lubricants and means for adjusting the pH. All these ingredients are known in the art.

The propellant-gas-containing inhalable aerosols according to the invention may contain up to 5% by weight of active substance. Aerosols according to the invention contain, for example, 0.002 to 5% by weight, 0.01 to 3% by weight, 0.015 to 2% by weight, 0.1 to 2% by weight, 0.5 to 2% by weight or 0.5 to 1% by weight of active ingredient.

Alternatively topical administrations to the lung may also be by administration of a liquid solution or suspension formulation, for example employing a device such as a nebulizer, for example, a nebulizer connected to a compressor (e.g., the Pari LC-Jet Plus(R) nebulizer connected to a Pari Master(R) compressor manufactured by Pari Respiratory Equipment, Inc., Richmond, Va.).

The antibody of the invention can be delivered dispersed in a solvent, e.g., in the form of a solution or a suspension. It can be suspended in an appropriate physiological solution, e.g., saline or other pharmacologically acceptable solvent or a buffered solution. Buffered solutions known in the art may contain 0.05 mg to 0.15 mg disodium edetate, 8.0 mg to 9.0 mg NaCl, 0.15 mg to 0.25 mg polysorbate, 0.25 mg to 0.30 mg anhydrous citric acid, and 0.45 mg to 0.55 mg sodium citrate per 1 ml of water so as to achieve a pH of about 4.0 to 5.0. A suspension can employ, for example, lyophilised antibody.

The therapeutic suspensions or solution formulations can also contain one or more excipients. Excipients are well known in the art and include buffers (e.g., citrate buffer, phosphate buffer, acetate buffer and bicarbonate buffer), amino acids, urea, alcohols, ascorbic acid, phospholipids, proteins (e.g., serum albumin), EDTA, sodium chloride, liposomes, mannitol, sorbitol, and glycerol. Solutions or suspensions can be encapsulated in liposomes or biodegradable microspheres. The formulation will generally be provided in a substantially sterile form employing sterile manufacture processes.

This may include production and sterilization by filtration of the buffered solvent/solution used for the formulation, aseptic suspension of the antibody in the sterile buffered solvent solution, and dispensing of the formulation into sterile receptacles by methods familiar to those of ordinary skill in the art.

Nebulizable formulation according to the present disclosure may be provided, for example, as single dose units (e.g., sealed plastic containers or vials) packed in foil envelopes. Each vial contains a unit dose in a volume, e.g., 2 mL, of solvent/solutionbuffer.

The antibodies disclosed herein may to be suitable for delivery via nebulisation.

It is also envisaged that the antibody of the present invention may be administered by use of gene therapy. In order to achieve this, DNA sequences encoding the heavy and light chains of the antibody molecule under the control of appropriate DNA components are introduced into a patient such that the antibody chains are expressed from the DNA sequences and assembled in situ.

The present invention also provides an antibody molecule (or compositions comprising same) for use in the control of inflammatory diseases, for example acute or chronic inflammatory disease. Suitably, the antibody molecule (or compositions comprising same) can be used to reduce the inflammatory process or to prevent the inflammatory process. In one embodiment there is provided an in vivo reduction of activated T cells, in particular those involved in inappropriate inflammatory immune responses, for example recruited to the vicinity/location of such a response.

Reduction of activated T cells, as employed herein, may be a reduction, 10, 20, 30, 40, 50, 60, 70, 80, 90 or more percent in comparison to before treatment or without treatment. Advantageously, treatment with an antibody, fragment or composition according to the present invention, may allow the reduction in the level of activated T cells, without reducing the patients general level of T cells (unactivated T cells). This may result in fewer side effects, and possibly prevent T cell depletion in the patient.

The present invention also provides the antibody molecule of the present invention for use in the treatment or prophylaxis of a pathological disorder that is mediated by OX40 or associated with an increased level of OX40. The pathological condition, may, for example be selected from the group consisting of infections (viral, bacterial, fungal and parasitic), endotoxic shock associated with infection, arthritis, rheumatoid arthritis, asthma, COPD, pelvic inflammatory disease, Alzheimer's Disease, inflammatory bowel disease, Crohn's disease, ulcerative colitis, Peyronie's Disease, coeliac disease, gallbladder disease, Pilonidal disease, peritonitis, psoriasis, vasculitis, surgical adhesions, stroke, Type I Diabetes, lyme disease, arthritis, meningoencephalitis, autoimmune uveitis, immune mediated inflammatory disorders of the central and peripheral nervous system such as multiple sclerosis, lupus (such as systemic lupus erythematosus) and Guillain-Barr syndrome, Atopic dermatitis, autoimmune hepatitis, fibrosing alveolitis, Grave's disease, IgA nephropathy, idiopathic thrombocytopenic purpura, Meniere's disease, pemphigus, primary biliary cirrhosis, sarcoidosis, scleroderma, Wegener's granulomatosis, other autoimmune disorders, pancreatitis, trauma (surgery), graft-versus-host disease, transplant rejection, heart disease including ischaemic diseases such as myocardial infarction as well as atherosclerosis, intravascular coagulation, bone resorption, osteoporosis, osteoarthritis, periodontitis and hypochlorhydia.

In one embodiment the antibody according to the invention is employed in the treatment of allergy, COPD, autoimmune disease or rheumatoid arthritis.

The present invention also provides an antibody molecule according to the present invention for use in the treatment or prophylaxis of pain, particularly pain associated with inflammation.

The present invention further provides the use of an antibody molecule, fragment or composition according to the present invention in the manufacture of a medicament for the treatment or prophylaxis of a pathological disorder that is mediated by OX40 or associated with an increased level of OX40, in particular the pathological disorder is rheumatoid arthritis, asthma or COPD.

The present invention further provides the use of an antibody molecule, fragment or composition according to the present invention in the manufacture of a medicament for the treatment or prophylaxis of one or more medical indications described herein.

An antibody molecule, fragment or composition of the present invention may be utilised in any therapy where it is desired to reduce the effects of OX40 in the human or animal body. OX40 may be circulating in the body or may be present in an undesirably high level localised at a particular site in the body, for example a site of inflammation.

In one embodiment the antibody molecule of the present invention or a composition comprising the same is used for the control of inflammatory disease, e.g. as described herein.

The present invention also provides a method of treating human or animal subjects suffering from or at risk of a disorder mediated by OX40, the method comprising administering to the subject an effective amount of the antibody molecule of the present invention, or a composition comprising the same.

In one embodiment there is provided a process for purifiying an antibody (in particular an antibody or fragment according to the invention) comprising the steps:
performing anion exchange chromatography in non-binding mode such that the impurities are retained on the column and the antibody is eluted.

Suitable ion exchange resins for use in the process include Q.FF resin (supplied by GE-Healthcare). The step may, for example be performed at a pH about 8.

The process may further comprise an initial capture step employing cation exchange chromatography, performed for example at a pH of about 4 to 5, such as 4.5. The cation exchange chromatography may, for example employ a resin such as CaptoS resin or SP sepharose FF (supplied by GE-Healthcare). The antibody or fragment can then be eluted from the resin employing an ionic salt solution such as sodium chloride, for example at a concentration of 200 mM.

Thus the chromatograph step or steps may include one or more washing steps, as appropriate.

The purification process may also comprise one or more filteration steps, such as a dia filtration step.

A pI above 8, such as 8.5, 8.6, 8.7, 8.8 or 9.0 of the antibody or fragment is thought to assist the purification to provide the antibody or fragment "free" or "substantially free" from impurities, such as endotoxin, DNA and host cell proteins.

Thus in one embodiment there is provided a purified OX40 antibody or fragment, for example a humanised antibody or fragment, in particular an antibody or fragment according to the invention, in substantially purified from, in particular free or substantially free of endotoxin and/or host cell protein or DNA.

Purified form as used supra is intended to refer to at least 90% purity, such as 91, 92, 93, 94, 95, 96, 97, 98, 99% w/w or more pure.

Substantially free of endotoxin is generally intended to refer to an endotoxin content of 1 EU per mg antibody product or less such as 0.5 or 0.1 EU per mg product.

Substantially free of host cell protein or DNA is generally intended to refer to host cell protein and/or DNA content 400

μg per mg of antibody product or less such as 100 μg per mg or less, in particular 20 μg per mg, as appropriate.

The antibody molecule of the present invention may also be used in diagnosis, for example in the in vivo diagnosis and imaging of disease states involving OX40.

Comprising in the context of the present specification is intended to meaning including.

Where technically appropriate embodiments of the invention may be combined.

Embodiments are described herein as comprising certain features/elements. The disclosure also extends to separate embodiments consisting or consisting essentially of said features/elements.

The present invention is further described by way of illustration only in the following examples, which refer to the accompanying Figures, in which:

EXAMPLES

FIG. 1 in Detail a) Light chain V region of antibody A26 (SEQ ID NO:7)
b) Heavy chain V region of antibody A26 (SEQ ID NO:9)
c) CDRH1 (SEQ ID NO:1), CDRH2 (SEQ ID NO:2), CDRH3 (SEQ ID NO:3), CDRL1 (SEQ ID NO:4), CDRL2 (SEQ ID NO:5), CDRL3 (SEQ ID NO:6) of antibody A26) and CDRH2 (SEQ ID NO:20) and CDRL1 (SEQ ID NO:21) of antibody CA044_00026.
d) Light chain of antibody A26 (SEQ ID NO:11)
e) Light chain of antibody A26 including signal sequence (underlined) (SEQ ID NO:12)
f) Heavy chain of antibody A26 (SEQ ID NO:15)
g) Heavy chain of antibody A26 including signal sequence (underlined) (SEQ ID NO:16)
h) DNA encoding light chain variable region of antibody A26 (SEQ ID NO:8)
i) DNA encoding heavy chain variable region of antibody A26 (SEQ ID NO:10)
j) DNA encoding light chain of antibody A26 (SEQ ID NO:13)
k) DNA encoding light chain of antibody A26 including signal sequence (SEQ ID NO:14)
l) DNA encoding heavy chain of antibody A26 (SEQ ID NO:17)
m) DNA encoding heavy chain of antibody A26 including signal sequence (SEQ ID NO:18)
n) DNA encoding heavy and light chain of antibody A26 including signal sequences and intergenic sequence IGS2 (SEQ ID NO:19).

DNA Manipulations and General Methods

*E. coli* strain INVαF' (Invitrogen) was used for transformation and routine culture growth. DNA restriction and modification enzymes were obtained from Roche Diagnostics Ltd. and New England Biolabs. Plasmid preparations were performed using Maxi Plasmid purification kits (QIAGEN, catalogue No. 12165). DNA sequencing reactions were performed using the ABI Prism Big Dye terminator sequencing kit (catalogue No. 4304149) and run on an ABI 3100 automated sequencer (Applied Biosystems). Data was analysed using the program AutoAssembler (Applied Biosystems). Oligonucleotides were obtained from Invitrogen. Genes encoding initial V-region sequences were designed and constructed by an automated synthesis approach by Entelechon GmbH, and modified to generate the grafted versions by oligonucleotide directed mutagenesis. The concentration of Fab' was determined using Fab' assembly ELISA.

Example 1

Production and Humanisation of a Neutralising Anti-OX40 Antibody A26

Female Sprague Dawly rats were immunised with recombinant fusion protein of human OX40 and mFC. Antibody CA044_00026 which binds human OX-40 was isolated using the methods described in WO92/02551. Genes for the heavy chain variable domain (VH) and light chain variable domain (VL) of antibody CA044_00026 were isolated and sequenced following cloning via reverse transcription PCR.

A series of humanised VL and VH regions were designed using human V-region acceptor frameworks and by varying the number of donor residues in the framework regions. Two grafted VH regions (gH1 and 2) and 8 grafted VL regions (gL1-8) were designed and genes were built by oligonucleotide assembly and PCR mutagenesis.

Antibody Fab' fragments were constructed for each graft using the genes encoding the humanised variable domains which were sub-cloned into *E. coli* expression vector pTTOD, which contains DNA encoding the human Cγ1 heavy chain CH1 domain (G1 m17 allotype) and the human C kappa light chain constant domain (K1 m3 allotype) (as previously described in WO03/048208). The hinge region is truncated and modified, consisting of the sequence change from Cys-Pro-Pro-Cys to Cys-Ala-Ala to generate a hinge region with a single cysteine residue available for site specific attachment of a PEG moiety (see Example 2).

Sequences encoding the OmpA signal peptide were attached to the 5' end of the genes encoding both the heavy and light chains. On expression, the signal sequences target the transport of each polypeptide to the bacterial periplasm. Following translocation through the cell membrane the signal sequence is cleaved off, leaving the mature Fab' heavy & light chains.

The pTTOD vector containing each graft was transformed into the host strain *E. coli* K12 W3110 and the antibody Fab' fragments produced in *E. coli* by high cell density cultivation using standard methods. Antibodies were purified using cation exchange followed by anion exchange chromatography using standard methods (Humphreys et al., 2002, Protein Expression and Purification, 26, 309-320).

The various Fab' fragments produced were tested in the binding and blocking described hereinbelow and each was evaluated in terms of their expression in *E. coli*, their potency relative to the parent antibody, and their suitability for purification and downstream processing. This lead to the selection of graft gL8gH2 which was named A26. The V region sequences of this graft are shown in FIGS. 1 (*a*) and (*b*) and in SEQ ID NOs: 7 and 9 for the light chain (gL2) and heavy chains (gH2) respectively.

The heavy chain acceptor framework is the human germline sequence VH3 1-3 3-07 with framework 4 coming from this portion of the human JH-region germline JH4. The light chain acceptor framework is the human germline sequence VK1 2-1 1-02, with framework 4 coming from this portion of the human JK-region germline JK4. The amino acids at positions 37, 73, 78 and 94 (Kabat numbering) in the heavy chain of SEQ ID NO:9 are donor residues (from the parent antibody) which were found to be essential for retention of full potency. Residue 64 within CDRH2 was converted from the donor glutamate to the acceptor lysine (E64K) to create a molecule with a higher pI, more favourable for ion exchange purification. The amino acids at positions 64 and 71 (Kabat numbering) in the light chain of SEQ ID NO:7 are donor residues which were found to be essential for retention of full potency. Residues 27 and 28 within CDR-L1 were converted from the donor glutamate and aspartate to the acceptor glutamine (E27Q) and serine (D28S) to create a molecule with a higher pI, more favourable for ion exchange purification.

The CDRs of this antibody are shown in FIG. 1(c) as are the original CDRH2 (SEQ ID NO:20) and CDRL1 (SEQ ID NO:21) which are unmodified. The full-length light and heavy chains are shown in FIGS. 1(d) and (f) respectively.

The gL8 and gH2 genes were redesigned at the DNA level containing codons for both variable and constant regions optimized for expression in E. coli and expressed in the pTTOD(Fab') vector as described above. The DNA sequences encoding the light and heavy chains are shown in FIGS. 1(k), SEQ ID NO:14 and (m) SEQ ID NO:18 respectively.

The protein sequence of this Fab' (including the constant regions) is provided in SEQ ID NOS: 11 and 12 (light chain without and with OmpA signal peptide) and SEQ ID NOS: 15 and 16 (heavy chain without and with OmpA signal peptide). The pTTOD (A26 IGS2) dicistronic expression vector includes the sequence provided in FIG. 1 (n) and SEQ ID NO:19. The sequence contains an intergenic sequence, IGS2, between the light and heavy chain genes (See WO03/048208) and the OmpA leader sequence at the start of both the light and heavy chain genes.

Example 2

Production of A26Fab'-PEG

The Fab' fragment A26 produced in E. coli and purified as described in Example 1 was PEGylated according to the methods described in or WO2007/003898.

The PEG was attached to the hinge cysteine at position 226 (linear numbering) of the heavy chain (SEQ ID NO:15) such that a lysyl-maleimide group was attached to the cysteine residue at position 226 of the heavy chain (SEQ ID NO:15), and each amino group of the lysyl residue has covalently linked to it a methoxypoly(ethyleneglycol) residue having a molecular weight of about 20,000 Da. The total molecular weight of the PEG attached to the antibody was therefore approximately 40,000 Da, as shown in FIG. 2.

Example 3

Assessment of the Affinity of A26 and A26Fab'-PEG for OX40

The BIAcore technology monitors the binding between biomolecules in real time and without the requirement for labelling. One of the interactants, termed the ligand, is either immobilised directly or captured on the immobilised surface while the other, termed the analyte, flows in solution over the captured surface. The sensor detects the change in mass on the sensor surface as the analyte binds to the ligand to form a complex on the surface. This corresponds to the association process. The dissociation of the analyte from the ligand is monitored when the analyte is replaced by buffer. In the affinity BIAcore assay, the ligand is the antibody being tested and the analyte is human OX40.

Instrument: Biacore® 3000, Biacore AB, Uppsala, Sweden.

Sensor chip: CM5 (research grade) Catalogue Number: BR-1001-14, Biacore AB, Uppsala, Sweden. Chips were stored at 4° C.

Amine Coupling Kit: Catalogue Number: BR-1000-50, Biacore AB, Uppsala, Sweden Ethyl-3-(3-dimethylaminopropyl) carbodiimide hydrochloride (EDC). Made up to 75 mg/mL in distilled water and stored in 200 µL aliquots at −70° C.

N-Hydroxysuccinimide (NHS). Made up to 11.5 mg/mL in distilled water and stored in 200 aliquots at −70° C.

1 M Ethanolamine hydrochloride-NaOH pH 8.5. Stored in 200 µL aliquots at −70° C.

Buffers: Running buffer: HBS-EP (being 0.01 M HEPES pH 7.4, 0.15 M NaCl, 3 mM EDTA, 0.005% Surfactant P20). Catalogue Number: BR-1001-88, Biacore AB, Uppsala, Sweden. Buffer stored at 4° C.

Immobilisation buffer: Acetate 5.0 (being 10 mM sodium acetate pH 5.0). Catalogue number: BR-1003-51, Biacore AB, Uppsala, Sweden. Buffer stored at 4° C.

Ligand capture: Affinipure F(ab')$_2$ fragment goat anti-human IgG, F(ab')$_2$ fragment specific. Jackson ImmunoResearch Inc (Pennsylvania, USA) Catalogue number: 109-006-097. Reagent stored at 4° C.

Ligand: Antibodies A26 and A26Fab'-PEG, stored at 4° C.

Analyte: Human OX40 extracellular (185 aa) domain fused to the murine IgG2a Fc (232 aa). (0.5 mg/ml, Ancell No 513-020 lot 142805), stored at 4° C.

Regeneration Solution: 40 mM HCl prepared by dilution with distilled water from an 11.6 M stock solution (BDH, Poole, England. Catalogue number: 101254H).

5 mM NaOH prepared by dilution with distilled water from a 50 mM stock solution. Catalogue number: BR-1003-58, Biacore AB, Uppsala, Sweden.

Assay Method: The assay format was capture of the antibody by immobilised anti-human F(ab')$_2$ then titration of the human extracellular domain OX40 over the captured surface. An example of the procedure is given below:

BIA (Biamolecular Interaction Analysis) was performed using a BIAcore 3000 (BIAcore AB). Affinipure F(ab')$_2$ Fragment goat anti-human IgG, F(ab')$_2$ fragment specific (Jackson ImmunoResearch) was immobilised on a CM5 Sensor Chip via amine coupling chemistry to a capture level of ≈4000 response units (RUs). HBS-EP buffer (10 mM HEPES pH 7.4, 0.15 M NaCl, 3 mM EDTA, 0.005% Surfactant P20, BIAcore AB) was used as the running buffer with a flow rate of 10 µl/min. A 10 µl injection of Fab' at 0.5 µg/mL or Fab'-PEG at 50 µg/mL was used for capture by the immobilised anti-human IgG-F(ab')$_2$. Human OX40 was titrated over the captured antibody at various concentrations (25 nM to 0.78 nM) at a flow rate of 30 µL/min. The surface was regenerated by a 10 µL injection of 40 mM HCl, followed by a 5 µL injection of 5 mM NaOH at a flowrate of 10 µL/min.

Background subtraction binding curves were analysed using the BIAevaluation software (version 3.2) following standard procedures. Kinetic parameters were determined from the fitting algorithm.

The affinity value determined for A26 was in the range 19-45.4 pM and A26Fab'-PEG was in the range 13.7-50.3 pM.

The following table shows replicate data for unPEGylated humanised Fab fragment A26 (fab*) and A26 Fab'-PEG Fab fragment (Fab-PEG**), binding human OX40:

TABLE 1

| Sample | ka(1/Ms) | Kd(1/s) | KD(M) | KD(pM) |
|---|---|---|---|---|
| Fab* | 4.86 ± 1.6E+05 | 1.29 ± 0.07E−05 | 2.96E−11 | 29.6 |
| Fab-PEG** | 4.76 ± 2.1E+05 | 1.30 ± 0.46E−05 | 3.13E−11 | 31.3 |

*average of 5 determinations,
**average of 4 determinations

Example 3a

Cell-Based Affinity and Ligand-Blocking Capacity of A26Fab'-PEG

Cell-Based Affinity

To determine the affinity of A26Fab'-PEG for cell surface expressed antigen, saturation binding experiments were performed using activated CD4$^+$OX40$^+$ T cells, and FITC labeled antibody. Specific binding of antibody to receptor at equilibrium across a range of ligand concentrations was used to determine K$_D$, assuming that only a very small fraction of antibody was bound to receptor at any point on the binding curve.

Equilibrium binding is described using the following equation:

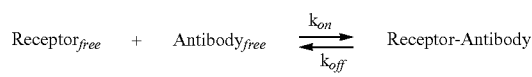

The rate of association of antibody with receptor=$k_{on}$×[Receptor$_{free}$]×[Antibody$_{free}$]

The rate of dissociation of receptor-antibody complex=$k_{off}$×[Receptor-Antibody]

At equilibrium, the association and dissociation rates are equal and an equation can be derived which describes the binding isotherm; on a semi-log plot the binding is sigmoidal. The K$_D$ is defined by k$_{off}$/k$_{on}$, and can be calculated from the binding curve as the concentration at which half-maximal binding occurs.

Figure 3:
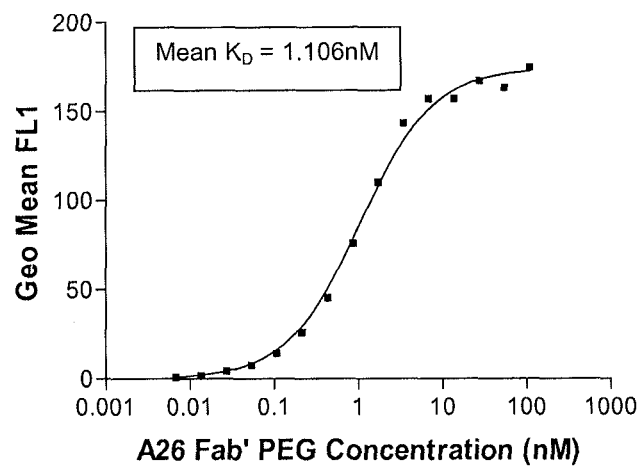
FIG. 3 shows the cell-based affinity of the A26 Fab'-PEG antibody for cell surface OX40

Binding of FITC labelled A26Fab'-PEG to activated human CD4$^+$OX40$^+$ T cells was measured by flow cytometry across a 4-log concentration range. A representative binding curve for A26Fab'-PEG is shown in FIG. 3. K$_D$ values obtained on activated cells from 3 different donors were 1.193 nM, 1.071 nM and 1.055 nM.

The cell-based K$_D$ of A26Fab'-PEG (mean 1.106 nM) is significantly weaker than the binding to recombinant OX40 measured by BIAcore (31.3 pM). This could be due to a number of factors. A26Fab'-PEG may have higher affinity for recombinant OX40 expressed as a dimeric Fc fusion protein, which has a different tertiary and quaternary structure than native cell surface expressed OX40, predicted to associate as a non-covalent trimer in the cell membrane (Chan et. al., 2000). Furthermore, the affinity may be altered by differential glycosylation of recombinant versus. native OX40. The 3-dimensional environment of the cell membrane such as membrane convolutions and co-localised proteins may also provide steric hindrance, limiting the accessibility of OX40 to A26Fab'-PEG. Consequently, the cell-based affinity probably represents a closer measurement of the true drug affinity in vivo.

Methods: A26Fab'-PEG Binding to Human Activated CD4$^+$OX40$^+$ T Cells.

PBMC were isolated by separation on a Ficoll gradient and activated with 1 µg/mL PHA-L for 3 days at 37° C., 5% CO$_2$, 100% humidity. CD4$^+$ T cells were isolated by negative selection using magnetic beads (CD4$^+$ T cell Isolation Kit II for Human; Miltenyi Biotec). Approximately 1.2×10$^5$ cells were incubated in the presence of antibody (final concentration range 10 µg/mL-0.0006 µg/mL (111 nM-0.0068 nM)) for 2 hours on ice. The cells were washed prior to analysis by flow cytometry using a FACScalibur (Becton Dickinson). Two titration curves were produced, one with A26Fab'-PEG and a second with gA33 Fab'-PEG as a non-specific binding control. Linear regression analysis was used to subtract non-specific binding and the specific binding curve thus generated was analysed by non-linear regression (Graphpad Prism®) to determine K$_D$.

Example 3b

Ligand-Blocking Capacity

Figure 4:
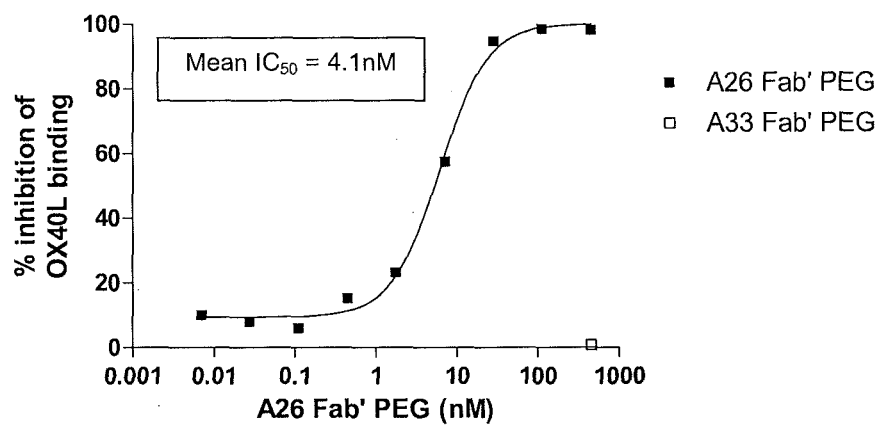
FIG. 4 shows percentage inhibition of OX40L binding to activated T cells by A26 Fab'-PEG antibody

The capacity of A26Fab'-PEG to block the interaction between cell-surface expressed OX40 and recombinant OX40L was measured using a flow cytometry-based ligand blocking assay. Briefly, activated human CD4$^+$OX40$^+$ T cells were pre-incubated with a titration of A26Fab'-PEG. Recombinant OX40L was subsequently added to the cells and allowed to bind in the presence of A26 Fab'-PEG. The proportion of OX40L bound was then detected by flow cytometry using a labelled secondary reagent. FIG. 4 shows a representative inhibition curve and demonstrates that A26Fab'-PEG is capable of completely blocking OX40L binding. The mean IC$_{50}$ for inhibition of recombinant OX40L binding was 4.1 nM (n=2 donors).

Methods: Inhibition of OX40L Binding to Human Activated CD4$^+$OX40$^+$ T Cells by A26Fab'-PEG.

PBMC were isolated by separation on a Ficoll gradient and activated with 1 µg/mL PHA-L for 3 days at 37° C., 5% CO$_2$, 100% humidity. 2.5×10$^5$ cells were incubated in the presence of antibody (final concentration range 20 µg/mL-0.0003 µg/mL (229 nM-0.0035 nM)) for 10 minutes on ice. OX40L (biotinylated CD252 muCD8, Ancell) was added at a final concentration of 2 µg/ml and incubated for a further 30 minutes on ice. Cells were washed and OX40L binding detected by incubation with PE-labelled streptavadin (Jackson Immunoresearch) prior to analysis by flow cytometry using a FACScalibur (Becton Dickinson). gA33 Fab'-PEG was used as a non-specific control. The inhibition curve was analysed by non-linear regression (Graphpad Prism®) to determine the IC$_{50}$. The data shown is from one representative donor of two.

Example 4

Potency of A26Fab'-PEG in Human Functional Assays

To assess its potency in blocking endogenous OX40-OX40L binding during cellular interactions, A26 Fab'-PEG was tested in a range of antigen-driven human T cell responses.

Example 4a

Mixed Lymphocyte Reaction

First developed in 1964 (Bach et al., 1964, Science 143, 813-814) the allogeneic mixed lymphocyte reaction (MLR) is an in vitro model of alloreactive T cell activation and proliferation (O'Flaherty et al., 2000, Immunology, 100, 289-299), using whole peripheral blood mononuclear cells (PBMCs) from two unrelated donors. Donor T cells are activated through recognition of allogeneic major histocompatibility complex (MHC) antigens on unrelated donor stimulator PBMCs, resulting in cellular proliferation and cytokine production (Lukacs et al., 1993, Am J Pathology, 143, 1179-1188). T lymphocyte alloreaction has been shown to be driven by both the allogeneic MHC antigen and bound peptide (Sherman et al., 1993, Annu. Rev. Immunol, 11, 385-402), suggesting an MLR response may be against both stimulator allogeneic MHC antigens and bound peptides. The magnitude of an MLR response correlates with the degree of MHC mis-matching between the responder-stimulator pair (Forrester et al., 2004, Corneal Transplantation: An Immunological Guide to the Clinical Problem, Imperial College Press, 66-67). An MLR response results in the proliferation of cells from the responding donor and the production of both $T_H1$ (IL-2, IFN-γ and TNF-α) and $T_H2$ (IL-4, IL-5, IL-10 and IL-13) T cell derived cytokines. The exact cytokine profile in an MLR is thought to be specific to the responder-stimulator pairing (Jordan et al., 2002, J. Immunol. Methods, 260, 1-14). MLR assays have been used widely in research to study T cell activation pathways and screen immunosuppressive drugs, and in clinical settings to assess immune function in acquired immune deficiency syndrome (AIDS) patients and predict possible donor organ rejection in transplant recipients (Bromelow et al., 2001, J. Immunol. Methods, 247, 1-8).

Figure 5:
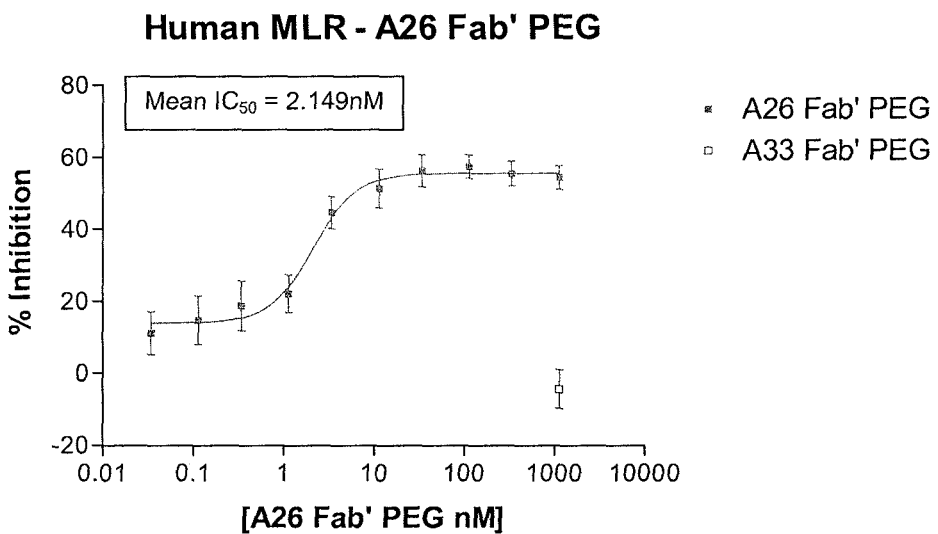
FIG. 5 shows percentage inhibition of T cell proliferation by A26 Fab'-PEG antibody in the human MLR

The effect of A26Fab'-PEG on in vitro human alloreactive T cell activation and proliferation was investigated using an MLR assay essentially as described by O'Flaherty et al., 2000. PBMCs from two unrelated donors were co-cultured in the presence and absence of A26Fab'-PEG and cellular proliferation measured by $^3$H-thymdine incorporation. As shown in FIG. 5, A26Fab'-PEG inhibited T cell proliferation in a dose dependent manner with an $IC_{50}$ value of 2.149 nM (0.1877 μg/mL) and a maximal inhibition of 57%. Supernatents from the human MLR were analysed in a Meso Scale Discovery (MSD) human cytokine assay to investigate the effect of A26 Fab'-PEG on cytokine production. A26Fab'-PEGylated partially inhibited production of IFN-γ (55% inhibition), IL-13 (50% inhibition) and IL-5 (80% inhibition) in the MLR (data not shown).

Method: Inhibition of the Human Allogeneic One-Way Whole PBMC MLR Proliferative Response by A26Fab'-PEG.

Human PBMCs from two unrelated donors were isolated from whole blood. Cells from one donor were inactivated by γ-irradiation to generate the stimulator population. Cells from the remaining donor formed the responder population. Stimulator and responder populations were mixed at a 1:1 ratio ($1\times10^5$ cells/donor) and cultured in the presence A26Fab'-PEG (1 ng-100 μg/mL) for 6 days. A33 Fab'-PEG (in-house reagent) was utilized as a control reagent. Cellular proliferation was measured at day 6 by $^3$H-thymidine incorporation (0.5 μCi/well). Data is displayed as percentage inhibition relative to the responder plus stimulator response in the absence of biologic reagent, and is the combined data from 10 different donor pairings (mean±SEM). $IC_{50}$ values were calculated using Graphpad Prism® software. The results are shown in FIG. 5.

Example 4b

Tetanus Toxoid Response

Figure 6:
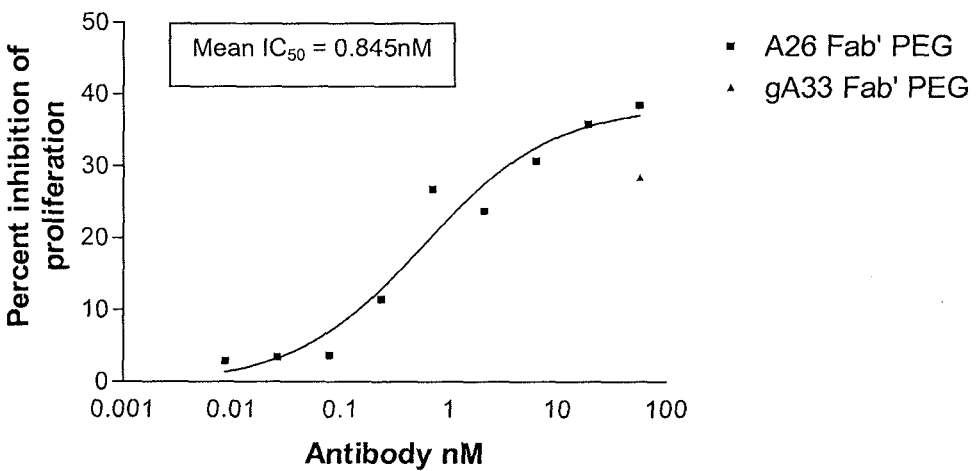
FIG. 6 shows A26 Fab'-PEG inhibition of proliferation of PBMC exposed to Tetanus Toxoid

Tetanus toxoid (TT) induces strong T cell specific immune responses in vaccinated individuals. In vitro, antigen-specific recall responses to TT challenge can be detected by monitoring proliferation and cytokine production ($T_H1$ & $T_H2$) from PBMC (Bishop et al., 2005). A26Fab'-PEG inhibited proliferation and IL-5, IL-13, IFN-γ and TNF-α production (data not shown) in a dose-dependent manner, with maximal inhibition of proliferation reaching 38%. $IC_{50}$ values for inhibition of proliferation, calculated for 2 donors, were 0.58 nM (0.051 μg/mL) and 1.11 nM (0.097 μg/mL). FIG. 6 shows the A26Fab'-PEG proliferation inhibition curve for 1 donor.

Method: A26 Fab'-PEG Inhibits Proliferation of PBMC Exposed to Tetanus Toxoid.

PBMC were isolated by separation on a Ficoll gradient and exposed to 1 μg/mL Tetanus Toxoid (Calbiochem) in the presence of A26Fab'-PEG (concentration range 5 μg/mL to 0.001 μg/mL) in a final volume of 200 μL per well in a 96-well round-bottomed plate. After 5 days incubation at 37° C., 5% $CO_2$, 100% humidity, cell proliferation was measured by incorporation of $^3$H thymidine (0.5 μCi/well) into actively dividing cells. Results from a single representative donor are presented. $IC_{50}$ values were calculated using Graphpad Prism® software.

Example 4c

House Dust Mite Response

Figure 7:
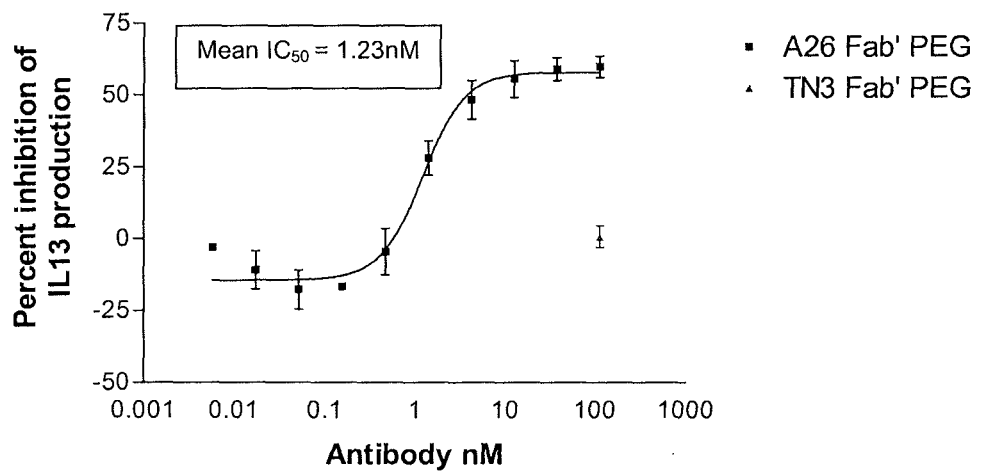
FIG. 7 shows A26 Fab'-PEG percentage inhibition of IL-13 production from PBMCs exposed to *Dermatophagoides pteronyssinus* allergenic extract

Severe acute asthma can be triggered by inhaled antigens such as house dust mite (Tillie-Leblond et al., 2005, Allergy, 60, (1), 23-29), including species from the genus *Dermatophagoides pteronyssinus*. Such allergens induce proliferative responses by peripheral blood cells and $T_H2$ polarised cytokine production, in atopic but not non-atopic patients (Ling et al., 2004, Lancet, 363, 608-615). An in vitro assay was set up to determine the effect of OX40 blockade on production of the $T_H2$ cytokine IL-13 in response to antigen challenge. PBMCs were taken from atopic people with an allergen-specific IgE (RAST) score between 3 and 5 (scale 0 to 6) and stimulated with *Dermatophagoides pteronyssinus* antigen in the presence of A26Fab'-PEG or control antibody. A26Fab'-PEG inhibited IL-13 production to a maximum of 60% with an $IC_{50}$ value of 1.23 nM (FIG. 7). Furthermore, A26 Fab'-PEG also potently inhibited production of the cytokines IL-4, IL-5 and TNF-α in this assay whilst enhancing levels of the regulatory cytokine IL-10 (FIG. 8).

Method FIG. 7: A26Fab'-PEG Inhibits IL-13 Production from PBMC Exposed to *Dermatophagoides Pteronyssinus* Allergenic Extract.

PBMC were isolated from allergic volunteers by separation on a Ficoll gradient. Purified PBMC were exposed to 25 μg/mL *Dermatophagoides pteronyssinus* allergenic extract (Greer) in the presence of test antibody (concentration range 10 μg/mL to 0.0005 μg/mL) in a final volume of 200 μL per well in a 96-well round-bottomed plate. After 6 days incubation at 37° C., 5% $CO_2$, 100% humidity, supernatants were harvested and assayed for IL-13 content by ELISA (Biosource). The graph represents pooled data from three donors (mean±SEM). $IC_{50}$ values were calculated using Graphpad Prism® software.

Figure 8:
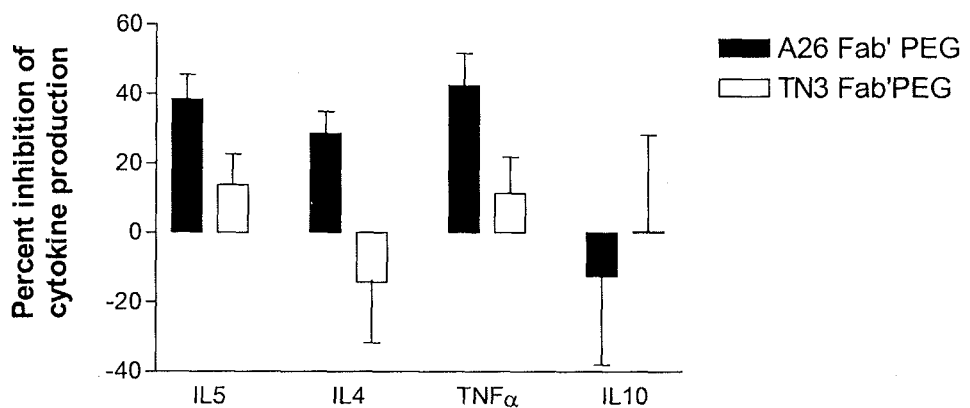
FIG. 8 shows A26 Fab'-PEG percentage inhibition of cytokine production from PBMCs exposed to *Dermatophagoides pteronyssinus* allergenic extract

Method FIG. 8: A26Fab'-PEG Modulates Cytokine Production from PBMC Exposed to *Dermatophagoides Pteronyssinus* Allergenic Extract.

PBMC were isolated from allergic volunteers by separation on a Ficoll gradient. Purified PBMC were exposed to 25 μg/mL *Dermatophagoides pteronyssinus* allergenic extract (Greer) in the presence of 10 μg/mL A26Fab'-PEG (114 nM) or control (TN3 Fab'-PEG) in a final volume of 200 μL per well in a 96-well round-bottomed plate. After 6 days incubation at 37° C., 5% $CO_2$, 100% humidity, supernatants were harvested and assayed for cytokine content using a multi-spot assay (MSD). The graphs represent pooled data from three donors (mean±SEM).

Summary

The $IC_{50}$ values for A26Fab'-PEG in human functional assays are summarised in Table 2. The potency of A26Fab-PEG is similar across all three assays and correlates well with the cell-based affinity measurement of 1.106 nM. In these assays, either cellular proliferation and/or production of multiple inflammatory cytokines was significantly suppressed, demonstrating that A26Fab'-PEGy profoundly inhibits T cell activation. The Tetanus Toxoid and House Dust Mite assays both measure recall responses by memory T cells, signifying that A26Fab'-PEG is capable of inhibiting established T cell responses to a variety of antigens.

TABLE 2

Mean $IC_{50}$ values for A26Fab'-PEG in human functional in vitro assays

| Functional Assay | Mean $IC_{50}$ (nM) | Mean $IC_{50}$ (µg/ml) |
| --- | --- | --- |
| Mixed Lymphocyte Reaction - Inhibition of Proliferation (n = 10) | 2.149 | 0.1877 |
| Tetanus Toxoid - Inhibition of Proliferation (n = 2) | 0.845 | 0.0733 |
| House Dust Mite - Inhibition of IL-13 production (n = 3) | 1.23 | 0.1067 |

The atopic memory $T_H2$ response to House Dust Mite antigen provides a relevant in vitro assay for allergic asthma and the data suggests that A26Fab'-PEG may be an effective therapy in this indication. OX40 co-stimulation has previously been linked to lung inflammation where it is suggested to play a critical role in both the differentiation of allergen-specific naïve CD4+ T cells into inflammatory $T_H2$ cells and the recall responses of memory $T_H2$ cells (Wang & Liu, 2007, J. Clin. Invest, 117 (12), 3655-3657). During allergic inflammation, the innate cytokine thymic stromal lyphopoietin (TSLP) produced by stressed epithelial cells drives maturation of human dendritic cells and induces expression of OX40L. OX40L functions to promote $T_H2$ polarisation of CD4+ T cells with an inflammatory phenotype of enhanced TNF-α but no IL-10 production (Ito et al, 2005, J. Exp. Med, 202 (9), 1213-1223). In the HDM response, A26 Fab'-PEG potently inhibited the classic $T_H2$ cytokines IL-13, IL-5 and IL-4 as well as TNF-α. Furthermore, in two out of four allergic donors A26Fab'-PEG enhanced IL-10 production. Thus, A26Fab'-PEG may have the capacity not only to inhibit allergic responses but also to modulate them towards a regulatory phenotype.

Example 5

A26Fab'-PEG Inhibits CD4+ & CD8+ T Cell Proliferation in a Hu-SCID Model

The Hu-SCID model involves reconstitution of SCID mice with human PBMCs which then elicit a strong xenogeneic response against the host mouse. This response is tracked by the proliferation of human T cells in the mouse. Using experimentally determined data on the PK of A26Fab'-PEG a dosing regime was designed which resulted in steady state plasma concentrations of 8, 23 and 34 µg/ml A26Fab'-PEG. The data in FIG. 9 demonstrates that CD4+ and CD8+ T cells are profoundly inhibited by maintaining steady state plasma levels of A26Fab'-PEG at 8, 23 and 34 µg/ml.

Method: A26Fab'-PEG Inhibits CD4+ and CD8+ T Cell Proliferation in a Hu-SCID Model.

Figure 9:
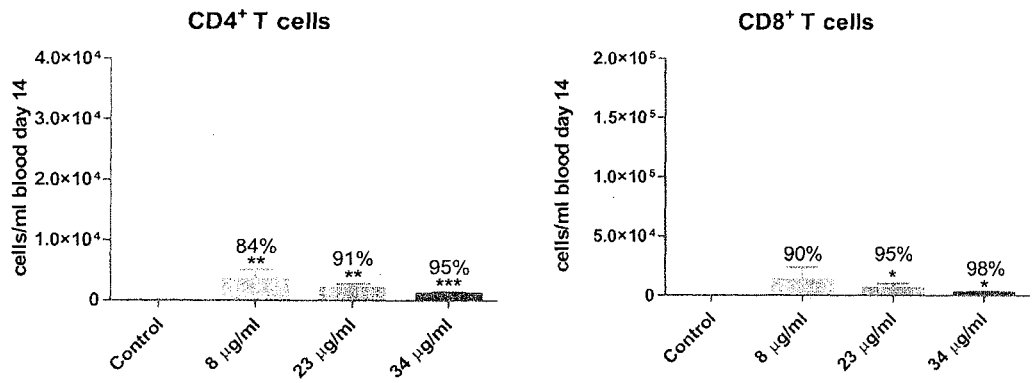
FIG. 9 shows A26 Fab'-PEG inhibits CD4+ and CD8+ T cell proliferation in a Hu-SCID model.

Mice were given a s.c. loading dose of 0.825, 2.475 or 8.25 mg/kg on day -2 and then daily s.c. maintenance doses of 0.25, 0.75 or 2.5 mg/kg respectively. Mice are depleted of NK cells by dosing with TMβ1 one day prior to transfer of eight million human PBMCs into the peritoneal cavity on day 0. The experiment is then terminated on day 14 and blood, peritoneal lavage fluid and spleen homogenate are analysed for CD4+ & CD8+ cells. Day 14 mice were killed by cervical dislocation & bled by cardiac puncture. The number of human CD4+ & CD8+ cells was then determined by FACS analysis. Data (n=10) is expressed as means±SEM. The decrease in CD4+ & CD8+ cells in the blood after administration of A26Fab'-PEG is shown in FIG. 9.

Example 6

Cross-Reactivity of A26Fab'-PEG with Non-Human Primate OX40

To validate use of A26Fab'-PEG in non-human primate (NHP) disease models and pre-clinical toxicology, its relative affinity and functional potency were compared on human & NHP cells.

Cell-Based Affinity on NHP Cells

Cynomolgus or rhesus CD4+ T cells were isolated from peripheral blood and activated to express high levels of OX40. The affinity of A26Fab'-PEG was measured by non-linear regression analysis of equilibrium binding curves as shown in FIG. 3. A26Fab'-PEG showed a less than 2-fold drop off in affinity for cynomolgus or rhesus CD4+ T cells as compared to human, indicating it is highly cross-reactive (Table 3).

TABLE 3

Cell-based affinity comparison of A26Fab'-PEG on human and NHP cells.

| A26 Fab'-PEG | $K_D$ (nM) |
| --- | --- |
| Human (n = 3) | 1.106 |
| Cynomolgus (n = 3) | 1.859 |
| Rhesus (n = 1) | 1.202 |

NHP PBMC were separated on a Lympholyte (VH Bio) gradient, activated with 1 µg/mL PHA-L for 3 days at 37° C., 5% $CO_2$, 100% humidity and CD4+ T cells were isolated by negative selection using magnetic beads (CD4+ T cell Isolation Kit II for non-human primate; MiltenyiBiotec). Affinities were measured as described in Example 3a (FIG. 3).

Example 7

Efficacy Study in the Cynomolgus Monkey CIA Model

Rationale for Study and Study Design

Cynomolgus collagen-induced arthritis is a standard model used to profile potential anti-arthritic drugs prior to human experimentation. In our hands, this model responds to treatments directed against TNFα and IL-6. These data are consistent with the clinical RA findings with equivalent anti-human therapeutics.

The induction of arthritis in cynomolgus monkeys requires two immunisation steps with collagen II separated by a period of 3 weeks. Arthritis symptoms (swelling and tenderness of one or more joints) can be manifest at any time after the second immunisation and were assessed weekly using an arthritis score. The experiment was run for 11 weeks in total. OX40 is a co-stimulation molecule and so interference with function would be expected to have effects on the immunisation phases of the model. Three dosing regimes with A26 Fab'-PEG were evaluated. One group received A26Fab'-PEG (100 mg/kg) once only on the day before first immunisation. A second group received A26 Fab'-PEG (100 mg/kg) once only on the day before the second immunisation and the third group received A26 Fab'-PEG (100 mg/kg) one day prior first and second immunisations. A control group of animals received an acetate buffer vehicle. Disease onset in the vehicle treated group was characterised by serum elevations in the acute phase proteins C-reactive protein (CRP) and haptoglobin, (biomarkers that are measured clinically in RA trials). Joint integrity was assessed by x-ray and by histological examination.

Results and Conclusion

Figure 10:
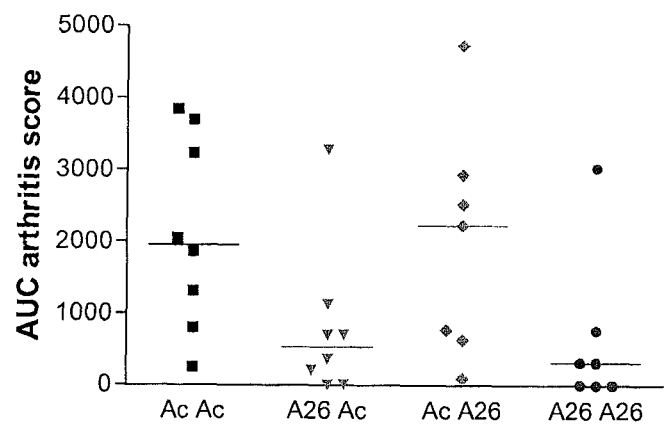
FIG. 10 shows inhibition of arthritis score (as area under the curve) by A26 Fab'-PEG in an in vivo model
Figure 11:
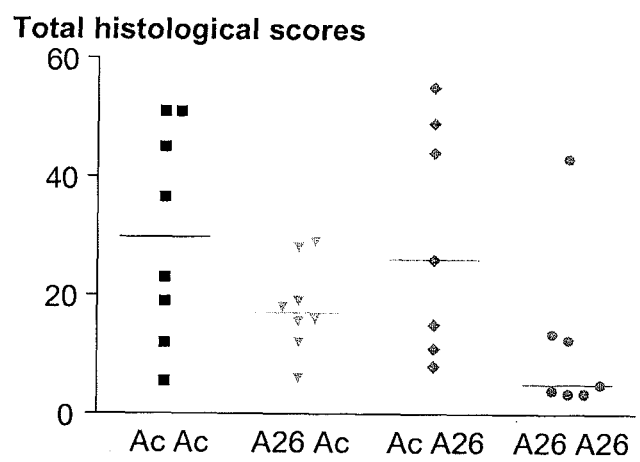
FIG. 11 shows total histololgical scores in an in vivo model for arthritis The original rat antibody from which the humanised antibodies are derived is referred to herein as CA044_00026.

In animals treated with A26Fab'-PEG on the day before first immunisation, arthritis severity was generally lower than in the vehicle treated group. These differences in arthritis score were statistically significant on days 49, 63 and 76. FIG. 10 shows an overall summary of the data for individual animals expressed as area under curve for clinical scores. X ray assessment of bone erosion to joints was also reduced (Table 4) as were histopathological changes (FIG. 11). Concentrations of CRP and haptoglobin tended to be lower than in the control group. Similar results were obtained for the group of animals dosed with A26Fab'-PEG one day prior to first immunisation and one day prior to second immunisation. However, there was no convincing anti arthritic effect observed in animals receiving A26Fab'-PEG once only on the day before second immunisation. These data show an anti arthritic effect of anti OX40 treatment in cynomolgus CIA and demonstrate the importance of OX40 to the initiation of the pathogenic immune response.

FIG. 10: Inhibition of Arthritis Score by A26 Fab'-PEG in Cynomolgus CIA.

Data shows individual animal area under the curve (AUC) for clinical score data for control animals receiving acetate buffer prior to first and second immunisations (Ac Ac), animals receiving prior to first immunisation (A26 Ac), animals receiving A26 Fab'-PEG prior to second immunisation (Ac A26) and animals receiving A26 Fab'-PEG prior to first and second immunisations (A26 A26). Bars are medians

TABLE 4

Effects of A26 Fab'-PEG treatment on x-ray scores of bone erosion

| Group | Day 0 | Day 35 | Day 76 |
| --- | --- | --- | --- |
| Ac Ac | 0 | 3.9 ± 1.7 | 24.8 ± 5.9 |
| A26 Ac | 0 | 0.3 ± 0.3 | 7.6 ± 3.9* |
| Ac A26 | 0 | 9.4 ± 4.5 | 17.9 ± 5.9 |
| A26 A26 | 0 | 0.9 ± 0.7 | 5.3 ± 4.8** |

Ac Ac animals received acetate buffer vehicle, A26 Ac animals received A26Fab'-PEG prior to first immunisation, Ac A26 animals received A26 Fab'-PEG prior to second immunisation and A26 A26 animals received A26 Fab'-PEG prior to first and second immunisations. Means ± s.e.m.,
*$p < 0.05$,
**$p < 0.01$ Wilcoxin's test.

Method FIG. 11: Reduction in Total Histological Score in Cynomolgus CIA by A26Fab'-PEG.

Data shows total histological scores (incorporating degeneration of cartilage and bone, fibrosis, granulation tissue and hyperplasia) for individual animals at termination of the study. Ac Ac animals received acetate buffer vehicle, A26 Ac animals received A26 Fab'-PEG prior to first immunisation, Ac A26 animals received A26Fab'-PEG prior to 2nd immunisation & A26A26 animals received A26 Fab'-PEG prior to $1^{st}$ & $2^{nd}$ immunisations. Bars are medians. It will of course be understood that the present invention has been described by way of example only, is in no way meant to be limiting, and that modifications of detail can be made within the scope of the claims hereinafter. Preferred features of each embodiment of the invention are as for each of the other embodiments mutatis mutandis. All publications, including but not limited to patents and patent applications, cited in this specification are herein incorporated by reference as if each individual publication were specifically and individually indicated to be incorporated by reference herein as though fully set forth.

What is claimed is:

1. An antagonistic antibody which binds human OX40 comprising a heavy chain and a light chain, wherein the variable domain of the heavy chain comprises a CDR having the sequence given in SEQ ID NO:1 for CDR-H1, a CDR having the sequence given in SEQ ID NO:2 or SEQ ID NO:20 for CDR-H2 and a CDR having the sequence given in SEQ ID NO:3 for CDR-H3 and wherein the variable domain of the light chain comprises a CDR having the sequence given in SEQ ID NO:4 or SEQ ID NO:21 for CDR-L1, the sequence given in SEQ ID NO:5 for CDR-L2 and the sequence given in SEQ ID NO:6 for CDR-L3.

2. An antibody according to claim 1 wherein the heavy chain comprises the sequence given in SEQ ID NO:9.

3. An antibody according to claim 1, wherein the light chain comprises the sequence given in SEQ ID NO:7.

4. An antagonistic antibody molecule according to claim 1, wherein the antibody molecule is selected from the group consisting of: a complete antibody molecule having full length heavy and light chains or a fragment thereof, including a Fab, modified Fab', Fab', F(ab')$_2$, Fv, VH, VL or scFv fragment.

5. An antagonistic antibody which binds human OX40, having a heavy chain comprising the sequence given in SEQ ID NO:9 and a light chain comprising the sequence given in SEQ ID NO:7.

6. An antagonistic antibody which binds human OX40, wherein the variable domain of the light chain comprises a sequence having at least 98% identity to the light chain variable domain of the antibody of claim 5 and wherein the variable domain of the heavy chain comprises a sequence having at least 98% identity to the heavy chain variable domain of the antibody of claim 5.

7. An antagonistic antibody which binds human OX40, having a heavy chain comprising the sequence given in SEQ ID NO:15 and a light chain comprising the sequence given in SEQ ID NO:11.

8. An antagonistic antibody which binds human OX40, in which the heavy and light chains comprise sequences having at least 98% identity to the corresponding heavy and light chains of the antibody of claim 7.

9. An antagonistic antibody molecule according to claim 1, that has been modified to enable an effector or reporter molecule to be attached to it.

10. An antagonistic antibody molecule according to claim 9, wherein the modification is the addition to the C-terminal end of its heavy chain of one or more amino acids to allow the attachment of an effector or reporter molecule.

11. The antagonistic antibody molecule of claim 10, wherein the additional amino acids form a modified hinge region containing one or two cysteine residues to which the effector or reporter molecule may be attached.

12. An antagonistic antibody molecule according to claim 1, having an effector or a reporter molecule attached to it.

13. An antagonistic antibody molecule according to claim 12, wherein the effector molecule comprises one or more polymers.

14. An antagonistic antibody molecule according to claim 13, wherein the one or more polymers is/are optionally substituted straight or branched chain polyalkylene, polyalkenylene or polyoxyalkylene polymer or a branched or unbranched polysaccharide.

15. An antagonistic antibody molecule according to claim 14, wherein the one or more polymers is/are a methoxypoly (ethyleneglycol) or poly(ethyleneglycol).

16. An antagonistic antibody molecule according to claim 15, having attached to one of the cysteine residues at the C-terminal end of the heavy chain a lysyl-maleimide or lysyl bismaleimide group wherein each amino group of the lysyl residue has covalently linked to it a methoxypoly(ethyleneglycol) residue having a molecular weight of about 20,000 Da.

17. An antagonistic antibody molecule having specificity for human OX40, which is a modified Fab fragment having a heavy chain comprising the sequence given in SEQ ID NO:15 and a light chain comprising the sequence given in SEQ ID NO:11 and having attached to the cysteine at position 226 of the heavy chain a lysyl-maleimide group wherein each amino group of the lysyl residue has covalently linked to it methoxypoly(ethyleneglycol) residue having a molecular weight of about 20,000 Da.

18. An antagonistic antibody having a binding affinity for isolated human OX40 of 100 pM or better.

19. An antagonistic antibody which binds human OX40 and which binds to the same epitope as the antibody of claim 5 with a binding affinity of 100 pM or better.

20. An antagonistic antibody which binds human OX40 which has a binding affinity for isolated human OX40 of 100 pM or better and cross-blocks the binding of the antibody of claim 5 to human OX40 or is cross-blocked from binding human OX40 by the antibody of claim 5.

21. An epitope on human OX40 bound by the antibody of claim 5.

22. An isolated DNA sequence encoding the heavy and/or light chain(s) of an antibody according to claim 1.

23. A cloning or expression vector comprising one or more DNA sequences according to claim 22.

24. A vector according to claim 23, wherein the vector comprises the sequences given in SEQ ID NO:14 and SEQ ID NO:18.

25. A vector according to claim 23, wherein the vector comprises the sequence given in SEQ ID NO:19.

26. A cultured host cell comprising one or more cloning or expression vectors according to claim 23.

27. A process for the production of an antibody, comprising culturing the host cell of claim 26 and isolating the antibody.

28. A pharmaceutical composition comprising an antibody according to claim 1, in combination with one or more of a pharmaceutically acceptable excipient, diluent or carrier.

29. A pharmaceutical composition according to claim 28, additionally comprising other active ingredients.

* * * * *

UNITED STATES PATENT AND TRADEMARK OFFICE
CERTIFICATE OF CORRECTION

PATENT NO.         : 8,614,295 B2                               Page 1 of 1
APPLICATION NO.    : 12/706993
DATED              : December 24, 2013
INVENTOR(S)        : Alastair David Griffiths Lawson et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 455 days.

Signed and Sealed this
Sixth Day of May, 2014

Michelle K. Lee
*Deputy Director of the United States Patent and Trademark Office*